(12) United States Patent
Nicolaides et al.

(10) Patent No.: US 7,223,598 B2
(45) Date of Patent: May 29, 2007

(54) METHODS FOR ISOLATING NOVEL ANTIMICROBIAL AGENTS FROM HYPERMUTABLE MAMMALIAN CELLS

(75) Inventors: Nicholas C. Nicolaides, Boothwyn, PA (US); Luigi Grasso, Philadelphia, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 0 days.

(21) Appl. No.: 11/235,037

(22) Filed: Sep. 26, 2005

(65) Prior Publication Data

US 2006/0068497 A1   Mar. 30, 2006

Related U.S. Application Data

(60) Division of application No. 10/369,845, filed on Feb. 19, 2003, now abandoned, which is a continuation of application No. 09/708,200, filed on Nov. 7, 2000, now Pat. No. 6,576,468.

(51) Int. Cl.
    *C12N 15/01* (2006.01)
(52) U.S. Cl. ..................................... 435/440
(58) Field of Classification Search ...................... None
    See application file for complete search history.

(56) References Cited

U.S. PATENT DOCUMENTS

| 5,885,827 | A  | 3/1999  | Wabl et al. ............... 435/320.1 |
| 5,907,079 | A  | 5/1999  | Mak et al. ....................... 800/2 |
| 6,146,894 | A  | 11/2000 | Nicolaides et al. ......... 435/440 |
| 6,191,268 | B1 | 2/2001  | Liskay et al. ............... 536/23.5 |
| 6,287,862 | B1 | 9/2001  | delCardayre et al. ....... 435/440 |
| 6,576,468 | B1 | 6/2003  | Nicolaides et al. ......... 435/455 |

FOREIGN PATENT DOCUMENTS

| CA | 2240609 | 10/1999 |
| WO | WO 97/05268 | 2/1997 |
| WO | WO 98/07833 | 2/1998 |
| WO | WO 99/19492 | 4/1999 |

OTHER PUBLICATIONS

Alderson, G. et al., "Physiology and genetics of antibiotic production and resistance", *Res. Microbiol.*, 1993, 144, 665-672.
Allen, D., et al., "MutS mediates heteroduplex loop formation by a translocation mechanism," *EMBO J.*, 1997, 16(14), 4467-4476.
Aronshtam, A., et al. "Dominant negative mutator mutations in the mutl gene of *Escherichia coli*", *Nucleic Acids Research*, 1996, 24(13), pp. 2498-2504.
Baker, S.M., et al., "Male mice defective in the DNA mismatch repair gene PMS2 exhibit abnormal chromosome synapsis in meiosis," *Cell*, 1995, 82, 309-319.
Bell, C.J., et al., "Assignment of 30 microsatellite loci to the linkage map of *arabidopsis*," *Genomics*, 1994, 19, 137-144.
Bevins, C.L., et al., "Antimicrobial Peptides", Ciba Foundation Symposium 186, John Wiley & Sons, 1994.
Bjornson, K., et al., "Modulation of MutS ATP hydrolysis by DNA cofactors," *Biochemistry*, 2000, 39, 3176-3183.
Bronner C.E., et al., "Mutation in the DNA mismatch repair gene homologue hMLH1 is associated with hereditary non-polyposis colon cancer," *Nature*, 1994, 368, 258-261.
Cascalho M, et al. "Mismatch repair co-opted by hypermutation", *Science*, 1998, 279(20), pp. 1207-1210.
Chakravarti, D. et al., "Relating aromatic hydrocarbon-induced DNA adducts and c-H-*ras* mutations in mouse skin papillomas: The role of apurinic sites", *Proc. Natl. Acad. Sci. USA*, Oct. 1995, vol. 92, pp. 10422-10426.
Culligan, K.M., et al., "DNA mismatch repair in plants," *Plant Physiol.*, 1997, 15, XP-002099372, 833-839.
de Wind, N., et al., "Inactivation of the mouse Msh2 gene results in mismatch repair deficiency, methylation tolerance, hyper-recombination, and predisposition to cancer," *Cell*, 1995, 82, 321-330.
Drummond, J.T., et al., "Isolation of an hMSH2-p160 heterodimer that restores DNA mismatch repair to tumor cells," *Science*, 1995, 268, 1909-1912.
Drummond, J.T., et al., "Cisplatin and adriamycin resistance are associated with mutlα and mismatch repair deficiency in an ovarian tumor cell line," *J. Biological Chemistry*, 1996, 271(33), 19645-19648.
Edelmann, W., et al., "Meiotic pachytene arrest in MLH1-deficient mice," *Cell*, 1996, 85, 1125-1134.
Eshleman, J.R., et al., "Mismatch repair defects in human carcinogenesis," *Human Molecular Genetics*, 1996, 5, 1489-1494.
Fishel, R., et al., "The Human mutator gene homolog MSH2 and its association with hereditary nonpolyposis colon cancer," *Cell*, 1993, 7, 1027-1038.
Galio, L., et al., "ATP hydrolysis-dependent formation of a dynamic ternary nucleoprotein complex with MutS and MutL," *Nucleic Acids Research*, 1999, 27(11), 2325-2331.
Jean, M., et al., "Isolation and characterization of *AtMLH1*, a *MutL* homologue from *Arabidopsis thaliana*," *Mol. Gen. Genet.*, 1999, 262, XP-000986134, 633-642.
Harfe, B.D., "DNA mismatch repair and genetic instability," *Annu. Rev. Genet.*, 2000, 34, 359-399.

(Continued)

Primary Examiner—Nancy Vogel
(74) Attorney, Agent, or Firm—Woodcock Washburn LLP

(57) ABSTRACT

Dominant-negative alleles of human mismatch repair genes can be used to generate hypermutable cells and organisms. By introducing these genes into mammalian cells new cell lines with novel and useful properties can be prepared more efficiently than by relying on the natural rate of mutation or introduction of mutations by chemical mutagens. These methods are useful for generating novel and highly active antimicrobial molecules as well as superior antimicrobial agents from pre-existing chemicals. These methods are also useful for generating cell lines expressing novel antimicrobials that are useful for pharmaceutical manufacturing.

7 Claims, 6 Drawing Sheets

OTHER PUBLICATIONS

Hamilton, S.R., et al., "The molecular basis of turcot's syndrome," *N. Eng. J. Med.*, 1995, 332(13), 839-847.

Hoang J., et al., "BAT-26, an Indicator of the Replication Error Phenotype in Colorectal Cancers and Cell Lines", *Cancer Res.*, 1997, 57, 300-303.

Honma, M. et al., "Cytotoxic and Mutagenic Responses to X-rays and Chemical Mutagens in Normal and p53-mutated Human Lymphoblastoid Cells", *Mut. Res.*, 1997, 374, 89-98.

Huttner, K.M. et al., "Antimicrobial Peptides as Mediators of Epithelial Host Defense", *Pediatr. Res.*, 1999, 45(6), 785-794.

Jiricny, J., et al., "Mismatch repair defects in cancer," *Curr. Opin. Genet. Dev.*, 2000, 10, 157-161.

Kang, Y.K., et al., "Synthesis and Antibacterial Activity of New Carbapenems Containing Isoxazole Moiety", *Bioorg. Med. Chem. Lett.*, 2000, 10(2), 95-99.

Karran, P., et al., "Genomic instability and tolerance to alkylating agents," *Cancer Surveys*, 1996, 28, 69-71.

King, D.E. et al., "New Classification and Update on the Quinolone Antibiotics", *Am. Fam. Physician*, 2000, 61(9), 2741-2748.

Kong, Q., "PMS2-deficiency diminishes hypermutation of a $\lambda_1$ transgene in young but not older mice," *Molecular Immunology 36*, 1999, 83-91.

Leach, F.S., et al., "Mutations of mutS homolog in hereditary nonpolyposis colorectal cancer," *Cell*, 1993, 75, 1215-1225.

Lipkin, S.M., et al., "MLH3: a DNA mismatch repair gene associated with mammalian microsatellite instability," *Nature Genetics*, 2000, 24, XP-002165243, 27-35.

Liu, T., et al., "Microsatellite instability as a predictor of a mutation in a DNA mismatch repair gene in familial colorectal cancer," *Genes, Chromosomes & Cancer*, 2000, 27, 17-25.

Liu et al., "Analysis of Mismatch Repair Genes in Hereditary Non-polyposis Colorectal Cancer Patients", *Nature Medicine*, Feb. 1996, 2(2), 169-174.

Ma et al., "Dominant Negative Expression of hpMS2 Creates Isogenic Mismatch Repair Deficient Human Colon Cancer Cell Lines ", *Proc. Am. Assoc. Cancer Res.*, Mar. 1998, 39, p. 460 (Abstract #3130).

Matsuzaki K., "Why and how are peptide-lipid interactions utilized for self-defense? Magainins and tachyplesins as archetypes", *Biochim. Biophys. Acta*, 1999, 1462(1-2), 1-10.

McCallum, C.M., "Targeted screening for induced mutations," *Nature Biotechnology*, 2000, 18, 455-457.

Modrich, P., "Mismatch repair, genetic stability, and cancer," *Science*, 1994, 266, 1959-1960.

Neuberger, M., et al., "Mice perform a human repertoire," *Nature*, 1997, 386, 25-26.

Nicolaides, N.C., et al., "The jun family members, c-jun and junD, transactivate that human c-myb, promotor via an Ap1-like element," *J. Biological Chemistry*, 1992, 267(27), 19655-19672.

Nicolaides, N.C., et al., "Genomic organization of the human *PMS2* gene family," *Genomics*, 1995, 30, 195-206.

Nicolaides, N.C., et al., "Positive autoregulation of c-*myb*, expression via Myb binding sites in the 5' flanking region of the human c-*myb* gene," *Molecular and Cellular Biology*, 1991, 11(12), 6166-6176.

Nicolaides, N.C., "A naturally occuring *hPMS2* mutation can confer a dominant negative nutator phenotype," *Mol. Cell. Biol.*, 1998, 18(3), 1635-1641.

Nicolaides, N.C., et al., "Analysis of the 5' region of *PMS2* reveals heterogeneous transcripts and a novel overlapping gene," *Genomics*, 1995, 29, 329-334.

Nicolaides, N.C., et al., "Mutations of two PMS homologues in hereditary nonpolyposis colon cancer," *Nature*, 1994, 371, 75-80.

Nicolaides, N.C., et al., "Molecular cloning of the N-Terminus of GTBP," *Genomics*, 1996, 31, 395-397.

Palombo, F., et al., "Mismatch repair and cancer," *Nature*, 1994, 367, 417.

Papadopoulos, N., et al., "Mutation of a *mutL* homolog in hereditary colon cancer," *Science*, 1994, 263, 1625-1629.

Papadopoulos, N., et al., "Mutations of *GTBP* in genetically unstable cells," *Science*, 1995, 268, 1915-1917.

Parsons, R., et al., "hypdermutability and mismatch repair deficiency in RER+ tumor cells," *Cell*, 1993, 75, 1227-1236.

Parsons, R., et al., "Mismatch repair deficiency in phenotypically normal human cells," *Science*, 1995, 268, 738-740.

Peinado, M.A., et al., "Isolation and characterization of allelic losses and gains in colorectal tumors by arbitrarily primed polymerase chain reaction," *Proc. Natl. Acad. Sci. USA*, 1992, 89, 10065-10069.

Perucho, M., et al., "Cancer of the microsatellite mutator phenotype," *Biol. Chem.*, 1996, 377, 675-684.

Polaczek, P., et al. "Functional genetic tests of DNA mismatch repair protein activity in *Saccharomyces cerevisiae*", *Gene*, 1998, 213(1-2), pp. 159-167.

Prolla, T.A., et al., "MLH1, PMS1, and MSH2 interactions during the initiation of DNA mismatch repair in yeast," *Science*, 1994, 265, 1091-1093.

Quian, Y. et al., "Molecular events after antisense inhibition of hMSH2 in a HeLa cell line", *Mutation Research*, Oct. 12, 1998, vol. 418, pp. 61-71.

Sass, P.M., "Antimicrobial peptides: Structure, function and therapeutic potential", *Curr. Opin. In Drug Discov. & Develop.*, 2000, 3(5), 646-654.

Schrader, C.E., et al., "Reduced isotype switching in splenic B cells from mice deficient in mismatch repair enzymes," *J. Exp. Med.*, 1999, 323-330.

Sitaram, N. et al. "Interaction of antimicrobial peptides with biological and model membranes: structural and charge requirements for activity", *Biochim. Biophys. Acta*, 1999, 1462(1-2), 29-54.

Spampinato, C., et al., "The MutL ATPase is required for mismatch repair," *J. Biological Chemistry*, 2000, 275(13), 9863-9869.

Strand, M., et al., "Destabilization of tracts of simple repetitive DNA in yeast by mutations affecting DNA mismatch repair," *Nature*, 1993, 365, 274-276.

Su, S., et al., "Mispair specificity of methyl-directed DNA mismatch correction In Vitro," *J. Biological Chemistry*, 1988, 263(14), 6829-6835.

Vora, K.A., et al., "Severe attenuation of the B celll immune response in Msh2-deficient mice," *J. Exp. Med.*, 1999, 189(3), 471-481.

Yu, Y. et al., "Adriamycin induces large deletions as a major type of mutation in CHO cells", *Mutation Research*, Nov. 1994, vol. 325, pp. 91-98.

Wheeler, J.M.D., et al., "The role of hypermethylation of the *hMLH1* promoter region in HNPCC versus MSI+sporadic colorectal cancers," *J. Med. Genet.*, 2000, 588-592.

Winter, D.B., et al., "Altered spectra of hypermutation in antibodies from mice deficient for the DNA mismatch repair protein PMS2," *Proc. Natl. Acad. Sci. USA*, 1998, 95, 6953-6958.

Zasloff, M., "Antibiotic peptides as mediators of innate immunity", Curr. Opin. Immunol., 1992, 41(1), 3-7.

Reynaud, C.-A., et al., "Mismatch repair and immunoglobulin gene hypermutation: did we learn something?," *Immunology Today*, 1999, 20(11), 522-527.

Wiesendanger, M., et al., "Somatic hypermutation, transcription, and DNA mismatch repair," *Cell*, 1998, 94, 415-418.

Maher, L. J. 3rd, "Prospects for the therapeutic use of antigene oligonucleotides," *Cancer Invest.*, 1996, 14(1), 66-82 [Abstract only].

Agrawal, S. et al., "Antisense therapeutics," *Curr. Opin. Chem. Biol.*, Aug. 1998, 2(4), 519-528 [Abstract only].

Hampel, A. "The hairpin ribozyme: discovery, two-dimensional model, and development for gene therapy," *Prog. Nucleic Acid Res. Mol. Biol.*, 1998, 58, 1-39 [Abstract only].

Fire, A. et al., "Potent and specific genetic interference by double-stranded RNA in *Caenorhabditis elegans*," *Nature*, Feb. 1998, 391(6669), 806-811 [Abstract only].

Cho-Chung, Y. S. et al, "Oligonucleotides as transcription factor decoys," *Curr. Opin. Mol. Ther.*, Jun. 1999, 1(3), 386-392 [Abstract only].

Nellen, W. et al., "What makes an mRNA anti-sense-itive?" *Trends Biochem Sci.*, Nov. 1993, 18(11), 419-423 [Abstract only].

Vaish, N. K. et al., "Recent developments in the hammerhead ribozyme field," *Nucleic Acids Res.*, Dec. 1998, 26(23), 5237-5242 [Abstract only].

Breaker, R. R. et al., "A DNA enzyme that cleaves RNA," *Chem. Biol.*, Dec. 1994, 1(4), 223-229 [Abstract only].

TK-mlg1 TK=psg

METHODS FOR ISOLATING NOVEL ANTIMICROBIAL AGENTS FROM HYPERMUTABLE MAMMALIAN CELLS

CROSS-REFERENCE TO RELATED APPLICATIONS

This is a divisional of U.S. application Ser. No. 10/369,845, filed Feb. 19, 2003 now abandoned, which is a continuation of U.S. application Ser. No. 09/708,200 filed Nov. 7, 2000, now U.S. Pat. No. 6,576,468, issued Jun. 10, 2003, both of which are incorporated by reference herein in their entireties.

FIELD OF THE INVENTION

The present invention is related to the area of antimicrobial agents and cellular production of those agents. In particular, it is related to the field of identification of novel antimicrobial agents by placing mammalian cells under selection in the presence of the microbe.

BACKGROUND OF THE INVENTION

For as long as man has shared the planet with microorganisms there have been widespread outbreaks of infectious disease and subsequent widespread mortality associated with it. Although microorganisms and man frequently share a symbiotic relationship, microorganisms can, under some conditions, lead to sickness and death. The discovery, wide use and dissemination of antibiotics to treat microbial infection in both human and animal populations over the last one hundred or so years has done much to control, and in some instances, eradicate some microbes and associated infectious disease. However, microbes have a strong propensity to evolve and alter their genetic makeup when confronted with toxic substances that place them under life and death selective pressures. Therefore, emerging infectious diseases currently pose an important public health problem in both developed as well as developing countries. Not only have microbes evolved to evade and defeat current antibiotic therapeutics, but also there are novel and previously unrecognized and/or characterized bacterial fungal, viral, and parasitic diseases that have emerged within the past two decades. Sass, Curr. Opin. in *Drug Discov. & Develop.* 2000, 3(5):646–654.

Since the accidental discovery of a penicillin-producing mold by Fleming there has been steady progress in synthesizing, isolating and characterizing new and more effective beta-lactam antibiotics. In addition to the great success of the beta-lactam family of antibiotics, the newer fluoroquinolones have a broad-spectrum of bactericidal activity as well as excellent oral bio-availability, tissue penetration and favorable safety and tolerability profiles. King et al., *Am. Fam. Physician*, 2000, 61, 2741–2748. A newly devised four-generation classification of the quinolone drugs accounts for the expanded antimicrobial spectrum of the more recently introduced fluoroquinolones and their clinical indications. The so-called first generation drugs, which include nalidixic acid, are capable of achieving minimal serum levels. The second-generation quinolones, such as ciprofloxacin, have an increased gram-negative and systemic activity. The third-generation drugs comprise pharmaceuticals such as levofloxacin and are have significant and expanded action against gram-positive bacteria and atypical pathogens. Finally, the fourth-generation quinolone drugs, which, to date, only includes trovofloxacin, are highly active against anaerobes in addition to the activity described for the third-generation drugs. Furthermore, the quinolone class of anti-microbial drugs can be divided based on their pharmacokinetic properties and bioavailability.

Mammalian epithelial surfaces are remarkable for their ability to provide critical physiologic functions in the face of frequent microbial challenges. The fact that these mucosal surfaces remain infection-free in the normal host suggests that highly effective mechanisms of host defense have evolved to protect these environmentally exposed tissues. Throughout the animal and plant kingdoms, endogenous genetically encoded antimicrobial peptides have been shown to be key elements in the response to epithelial compromise and microbial invasion. Zasloff, *Curr. Opin. Immunol.*, 1992, 4, 3–7; and Bevins, *Ciba Found. Symp.*, 1994, 186, 250–69. In mammals, a variety of such peptides have been identified, including the well-characterized defensins and cathelicidins and others (andropin, magainin, tracheal antimicrobial peptide, and PR-39; see Bevins, *Ciba Found. Symp.*, 1994, 186, 250–69 and references therein). A major source of these host defense molecules is circulating phagocytic leukocytes. However, more recently, it has been shown that resident epithelial cells of the skin and respiratory, alimentary, and genitourinary tracts also synthesize and release antimicrobial peptides. Both in vitro and in vivo data support the hypothesis that these molecules are important contributors to intrinsic mucosal immunity. Alterations in their level of expression or biologic activity can predispose the organism to microbial infection. Huttner et al., *Pediatr. Res.*, 1999, 45, 785–94.

Across the evolutionary scale species from insects to mammals to plants defend themselves against invading pathogenic microorganisms by utilizing cationic antimicrobial peptides that rapidly kill microbes without exerting toxicity to the host. Physicochemical peptide-lipid interactions provide attractive mechanisms for innate immunity as discussed below. Many of these peptides form cationic amphipathic secondary structures, typically alpha-helices and beta-sheets, which can selectively interact with anionic bacterial membranes via electrostatic interactions. Rapid, peptide-induced membrane permeabilization and subsequent cellular lysis is the result. Matsuzaki, *Biochim. Biophys. Acta*, 1999, 1462, 1–10.

The primary structures of a large number of these host-defense peptides have been determined. While there is no primary structure homology, the peptides are characterized by a preponderance of cationic and hydrophobic amino acids. The secondary structures of many of the host-defense peptides have been determined by a variety of techniques. Sitaram et al., *Biochim, Biophys. Acta*, 1999, 1462, 29–54. The acyclic peptides tend to adopt helical conformation, especially in media of low dielectric constant, whereas peptides with more than one disulfide bridge adopt beta-structures.

As described above, one reason for the rise in microbial drug resistance to the first line antimicrobial therapies in standard use today is the inappropriate and over-use of prescription antibiotics. Although bacteria are the most common organisms to develop drug-resistance, there are numerous examples of demonstrated resistance in fungi, viruses, and parasites. The development of a resistant phenotype is a complex phenomenon that involves an interaction of the microorganism, the environment, and the patient, separately as well as in combination. Sitaram et al., *Biochim. Biophys. Acta*, 1999, 1462, 29–54. The microorganism in question may develop resistance while under antibiotic selection or it may be a characteristic of the microbe prior to exposure to a given agent. There are a number of mechanisms of resistance to antibiotics that have been described, including genes that encode antibiotic resistance enzymes that are harbored on extrachromosomal plasmids as well as DNA elements (e.g. transposable elements) that can reside either extra-chromosomally or within the host genome.

Due to the ability of microorganisms to acquire the ability to develop resistance to antibiotics there is a need to continually develop novel antibiotics. Traditional methods to develop novel antibiotics have included medicinal chemistry approaches to modify existing antibiotics (Kang et al., *Bioorg. Med. Chem. Lett.*, 2000, 10, 95–99) as well as isolation of antibiotics from new organisms (Alderson et al., *Res. Microbiol.*, 1993, 144, 665–72). Each of these methods, however, has limitations. The traditional medicinal chemistry approach entails modification of an existing molecule to impart a more effective activity. The chemist makes a "best guess" as to which parts of the molecule to alter, must then devise a synthetic strategy, synthesize the molecule, and then have it tested. This approach is laborious, requires large numbers of medicinal chemists and frequently results in a molecule that is lower in activity than the original antibiotic. The second approach, isolation of novel antimicrobial agents, requires screening large numbers of diverse organisms for novel antimicrobial activity. Then, the activity must be isolated from the microorganism. This is not a small task, and frequently takes many years of hard work to isolate the active molecule. Even after the molecule is identified, it may not be possible for medicinal chemists to effectively devise a synthetic strategy due to the complexity of the molecule. Furthermore, the synthetic strategy must allow for a cost-effective synthesis. Therefore, a method that would allow for creation of more effective antibiotics from existing molecules or allow rapid isolation of novel antimicrobial agents is needed to combat the ever-growing list of antibiotic resistant organisms. The present invention described herein is directed to the use of random genetic mutation of a cell to produce novel antibiotics by blocking the endogenous mismatch repair activity of a host cell. The cell can be a mammalian cell that produces an antimicrobial agent naturally, or a cell that is placed under selective pressure to obtain a novel antimicrobial molecule that attacks a specific microbe. Moreover, the invention describes methods for obtaining enhanced antimicrobial activity of a cell line that produces an antimicrobial activity due to recombinant expression or as part of the innate capacity of the cell to harbor such activity.

In addition, the generation of genetically altered host cells that are capable of secreting an antimicrobial activity, which can be protein or non-protein based, will be valuable reagents for manufacturing the entity for clinical studies. An embodiment of the invention described herein is directed to the creation of genetically altered host cells with novel and/or increased antimicrobial production that are generated by a method that interferes with the highly ubiquitous and phylogenetically conserved process of mismatch repair.

The present invention facilitates the generation of novel antimicrobial agents and the production of cell lines that express elevated levels of antimicrobial activity. Advantages of the present invention are further described in the examples and figures described herein.

SUMMARY OF THE INVENTION

One embodiment of the present invention provides a method for generating genetically altered mammalian cells and placing the cells under direct microbial selection as a means to isolate novel antimicrobial agents. Another embodiment provides a method for identifying novel microbe-specific toxic molecules by altering the ability of the cell to correct natural defects that occur in the DNA during the process of DNA replication. Interference with this process, called mismatch repair, leads to genetically dissimilar sibling cells. These genetically dissimilar cells contain mutations, ranging from one mutation/genome to two or more mutations/genome, offer a rich population of cells from which to select for specific output traits, such as the novel ability to resist microbial insult. The genetically altered cell generated by manipulation of the mismatch repair process is then incubated with a microbe that is normally toxic to cells. Most of the cells will rapidly lose viability and die; however, a subset of resistant cells will have the capacity to resist the microbial insult. These cells express a molecule, protein or non-protein in structure, that imbues an antimicrobial activity to the newly selected mammalian clones. These newly created cells can be expanded in vitro and the new molecule isolated and characterized by standard methods that are well described it the art. The novel molecule(s) are then tested for their ability to kill or inhibit the growth of the microbe by standard microbial assays that are well described in the art. Finally, the novel cell line generated serves as an additional resource for large-scale production of the novel antimicrobial agent for use in clinical studies. The processes described herein are applicable to any mammalian cell and any microbe for which an antibiotic agent is sought.

The invention provides methods for rendering mammalian cells hypermutable as a means to generate antimicrobial agents.

The invention also provides methods for generating genetically altered cell lines that secrete enhanced amounts of a known or novel antimicrobial polypeptide.

The invention also provides methods for generating genetically altered cell lines that secrete enhanced amounts of a known or novel antimicrobial non-polypeptide based molecule.

The invention also provides methods for generating genetically altered cell lines that do not secrete enhanced amounts of an antimicrobial peptide or non-peptide molecule but rather have a cell-surface active molecule that detoxifies the microbe under test.

The invention also provides methods for producing an enhanced rate of genetic hypermutation in a mammalian cell and use of this as the basis to select for microbial-resistant cell lines.

The invention also provides methods of mutating a known antimicrobial encoding gene of interest in a mammalian cell as a means to obtain a molecule with enhanced bactericidal activity.

The invention also provides methods for creating genetically altered antimicrobial molecules in vivo.

The invention also provides methods for creating novel antimicrobial molecules from pre-existing antimicrobial molecules by altering the innate enzymatic or binding ability of the molecules by altering the mismatch repair system within the host mammalian cell.

The invention also provides methods for creating a novel anti-microbial polypeptide or non-polypeptide based molecule that has the capacity to bind in an irreversible manner to a microbe and thereby block binding of the pathogenic microbe to a host target organism and result in loss of viability of the microbe.

The invention also provides methods for creating a novel antimicrobial polypeptide or non-polypeptide based small molecule that can block microbial cell growth and/or survival.

The invention also provides methods for creating a novel antimicrobial polypeptide or non-polypeptide based biochemical that are able to irreversibly bind to toxic chemicals produced by pathogenic microbes.

The invention also provides methods for creating genetically altered antimicrobial molecules, either peptide of non-peptide based, that have enhanced pharmacokinetic properties in host organisms.

The invention also provides methods for creating genetically altered cell lines that manufacture an antimicrobial molecules, either peptide of non-peptide based, for use in large-scale production of the antimicrobial agent for clinical studies.

These and other aspects of the invention are described in the embodiments below. In one embodiment of the invention described, a method for making a microbial-sensitive mammalian cell microbe resistant by rendering the cell line hypermutable is provided. A polynucleotide encoding a dominant negative allele of a mismatch repair gene is introduced into an mammalian cell. The cell becomes hypermutable as a result of the introduction of the gene.

In another embodiment of the invention, an isolated hypermutable cell is provided. The cell comprises a dominant negative allele of a mismatch repair gene. The cell exhibits an enhanced rate of hypermutation.

In another embodiment of the invention, an isolated hypermutable cell is provided. The cell comprises a dominant negative allele of a mismatch repair gene. The cell exhibits an enhanced rate of hypermutation. The populations of cells generated by introduction of the mismatch repair gene are grown in the presence of microbes that are toxic to the wild type non-mutant cells. Cells are selected that are resistant to the microbe and the novel molecule(s) isolated and characterized for antimicrobial activity by standard methods well described in the art.

In another embodiment of the invention, an isolated hypermutable cell is described to create a novel antimicrobial molecule from a pre-existing antimicrobial molecule by altering the innate enzymatic or binding ability of the molecule.

In another embodiment of the invention, a method of creating a novel antimicrobial polypeptide or non-polypeptide based molecule that has the capacity to bind in an irreversible manner to a microbe and thereby block binding of the pathogenic microbe to a host target organism and result in loss of viability of the microbe.

In another embodiment of the invention, a method of creating a novel antimicrobial polypeptide or non-polypeptide based small molecule that can block microbial cell growth and/or survival is described.

In another embodiment of the invention, a method of creating a novel antimicrobial polypeptide or non-polypeptide based biochemical that are able to irreversibly bind to toxic chemicals produced by pathogenic microbes is described.

In another embodiment of the invention, a method is provided for introducing a mutation into a known endogenous gene encoding for an antimicrobial polypeptide or a non-protein based antimicrobial molecule as a means to create a more efficacious antimicrobial. A polynucleotide encoding a dominant negative allele of a mismatch repair gene is introduced into a cell. The cell becomes hypermutable as a result of the introduction of the gene. The cell further comprises an antimicrobial gene(s) of interest. The cell is grown and tested to determine whether the gene encoding for an antimicrobial is altered and whether the novel molecule is more active by standard microbiology assays well known in the art.

In another embodiment of the invention, a gene or genes encoding for an antimicrobial molecule is introduced into a mammalian cell host that is mismatch repair defective. The cell is grown, and then clones are analyzed for enhanced antimicrobial characteristics.

In another embodiment of the invention, a method is provided for producing new phenotypes of a cell. A polynucleotide encoding a dominant negative allele of a mismatch repair gene is introduced into a cell. The cell becomes hypermutable as a result of the introduction of the gene. The cell is grown and tested for the expression of new phenotypes where the phenotype is enhanced secretion of a novel or known antimicrobial polypeptide.

In another embodiment of the invention, a method is provided for producing new phenotypes of a cell. A polynucleotide encoding a dominant negative allele of a mismatch repair gene is introduced into a cell. The cell becomes hypermutable as a result of the introduction of the gene. The cell is grown and tested for the expression of new phenotypes where the phenotype is enhanced secretion of a novel or known antimicrobial non-polypeptide based molecule.

In another embodiment of the invention, a method is provided for producing new phenotypes of a cell. A polynucleotide encoding a dominant negative allele of a mismatch repair gene is introduced into a cell. The cell becomes hypermutable as a result of the introduction of the gene. The cell is grown and tested for the expression of new phenotypes where the phenotype is enhanced antimicrobial activity of a novel or known antimicrobial polypeptide that is not secreted.

In another embodiment of the invention, a method is provided for producing new phenotypes of a cell. A polynucleotide encoding a dominant negative allele of a mismatch repair gene is introduced into a cell. The cell becomes hypermutable as a result of the introduction of the gene. The cell is grown and tested for the expression of new phenotypes where the phenotype is enhanced antimicrobial activity of a novel or known antimicrobial non-polypeptide based molecule that is not secreted.

In another embodiment of the invention, a method is provided for restoring genetic stability in a cell containing a polynucleotide encoding a dominant negative allele of a mismatch repair gene. The expression of the dominant negative mismatch repair gene is suppressed and the cell is restored to its former genetic stability.

In another embodiment of the invention, a method is provided for restoring genetic stability in a cell containing a polynucleotide encoding a dominant negative allele of a mismatch repair gene and a newly selected phenotype. The expression of the dominant negative mismatch repair gene is suppressed and the cell restores its genetic stability and the new phenotype is stable.

These and other embodiments of the invention provide the art with methods that generate enhanced mutability in cells and animals as well as providing cells and animals harboring potentially useful mutations and novel protein and non-protein based molecules.

Figure 1:
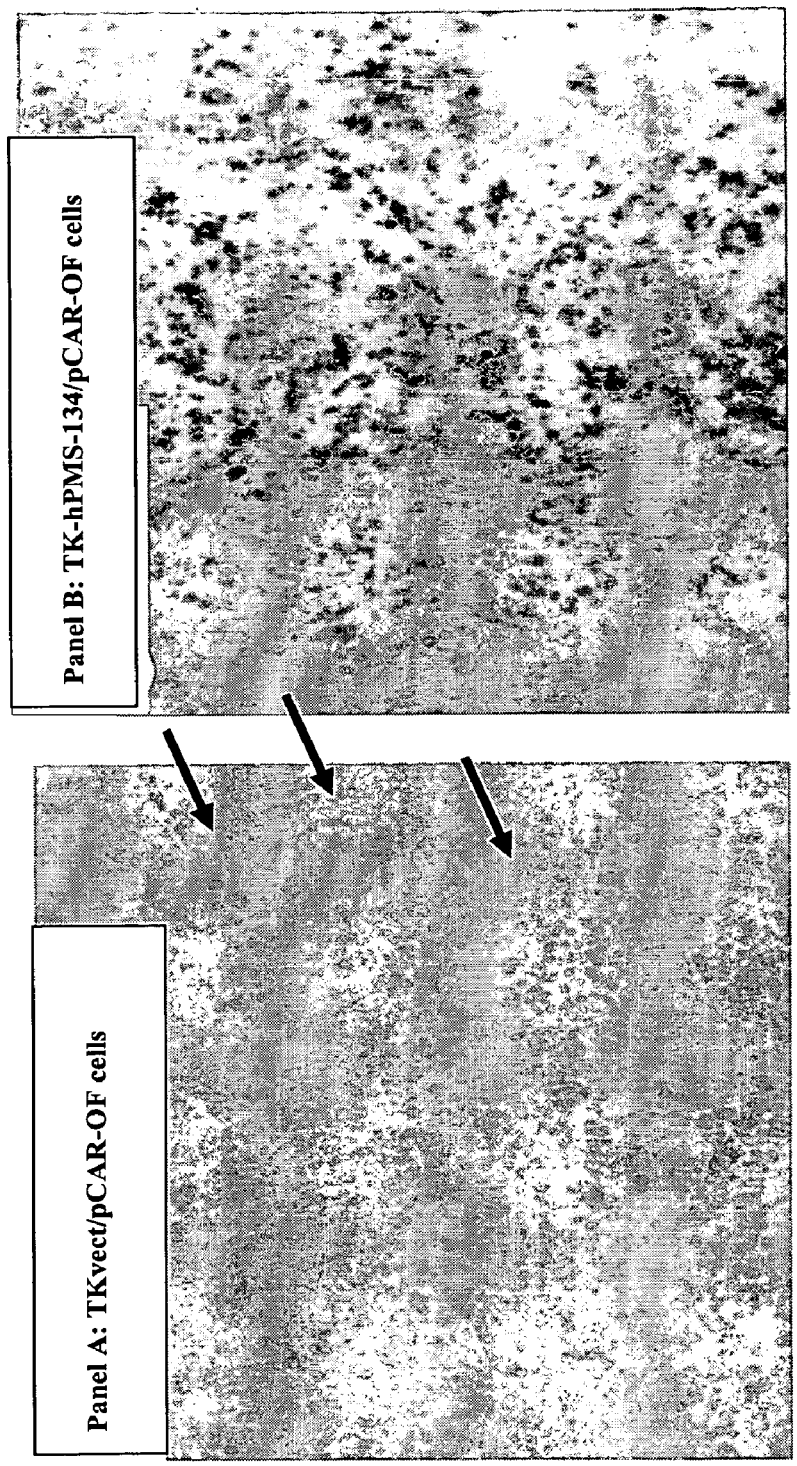
FIG. 1 is a representative in situ β-galactosidase staining of TK-hPMS2-134 or TKvect cells to measure for cells containing genetically altered β-galactosidase genes; arrows indicate Blue (β-galactosidase positive) cells.

The presented invention is directed to, in part, methods for developing hypermutable mammalian cells by taking advantage of the conserved mismatch repair process of host cells. Mismatched repair process is described in several references. Baker et al., *Cell*, 1995, 82, 309 319; Bronner et al., *Nature*, 1994, 368, 258 261; de Wind et al., *Cell*, 1995, 82, 321 330; and Drummond et al., *Science*, 1995, 268, 1909 1912. Dominant negative alleles of such genes, when introduced into cells or transgenic animals, increase the rate of spontaneous mutations by reducing the effectiveness of DNA repair and thereby render the cells or animals hypermutable. Hypermutable cells or animals can then be utilized to develop new mutations in a gene of interest or in a gene whose function has not been previously described. Blocking mismatch repair in cells such as, for example, mammalian cells or mammalian cells transfected with genes encoding for specific antimicrobial peptides or non-peptide based antimicrobials, can enhance the rate of mutation within these cells leading to clones that have novel or enhanced antimicrobial activity or production and/or cells that contain genetically altered antimicrobials with enhanced biochemical activity against a range of opportunistic microbes.

The process of mismatch repair, also called mismatch proofreading, is carried out by protein complexes in cells ranging from bacteria to mammalian cells. Modrich, *Science*, 1994, 266, 1959 1960. A mismatch repair gene is a gene that encodes for one of the proteins of such a mismatch repair complex. Baker et. al., Cell, 1995, 82, 309 319; Bronner et al., *Nature*, 1994, 368, 258 261; de Wind et al., *Cell*, 1995, 82, 321 330; Drummond et al., *Science*, 1995, 268, 1909 1912; and Modrich, *Science*, 1994, 266, 1959 1960. Although not wanting to be bound by any particular theory of mechanism of action, a mismatch repair complex is believed to detect distortions of the DNA helix resulting from non-complementary pairing of nucleotide bases. The non-complementary base on the newer DNA strand is excised, and the excised base is replaced with the appropriate base that is complementary to the older DNA strand. In this way, cells eliminate many mutations, which occur as a result of mistakes in DNA replication.

Dominant negative alleles cause a mismatch repair defective phenotype even in the presence of a wild-type allele in the same cell. An example of a dominant negative allele of a mismatch repair gene is the human gene hPMS2-134, which carries a truncation mutation at codon 134. Nicolaides et al., *Mol. Cell. Biol.*, 1998, 18, 1635–1641. The mutation causes the product of this gene to abnormally terminate at the position of the 134th amino acid, resulting in a shortened polypeptide containing the N-terminal 133 amino acids. Such a mutation causes an increase in the rate of mutations that accumulate in cells after DNA replication. Expression of a dominant negative allele of a mismatch repair gene results in impairment of mismatch repair activity, even in the presence of the wild-type allele. Any allele, which produces such effect, can be used in this invention.

Dominant negative alleles of a mismatch repair gene can be obtained from the ells of humans, animals, yeast, bacteria, or other organisms. Prolla et al., *Science*, 1994, 264, 1091 1093; Strand et al., *Nature*, 1993, 365, 274 276; and Su et al., *J. Biol. Chem.*, 1988, 263, 6829 6835. Screening cells for defective mismatch repair activity can identify such alleles. Cells from animals or humans with cancer can be screened for defective mismatch repair. Cells from colon cancer patients may be particularly useful. Parsons et al., *Cell,* 1993, 75, 1227 1236; and Papadopoulos et al., *Science,* 1993, 263, 1625 1629. Genomic DNA, cDNA, or mRNA from any cell encoding a mismatch repair protein can be analyzed for variations from the wild type sequence. Perucho, *Biol. Chem.,* 1996, 377, 675 684. Dominant negative alleles of a mismatch repair gene can also be created artificially, for example, by producing variants of the hPMS2-134 allele or other mismatch repair genes. Various techniques of site-directed mutagenesis can be used. The suitability of such alleles, whether natural or artificial, for use in generating hypermutable cells or animals can be evaluated by testing the mismatch repair activity caused by the allele in the presence of one or more wild-type alleles, to determine if it is a dominant negative allele.

A cell or an animal into which a dominant negative allele of a mismatch repair gene has been introduced will become hypermutable. This means that the spontaneous mutation rate of such cells or animals is elevated compared to cells or animals without such alleles. The degree of elevation of the spontaneous mutation rate can be at least 2-fold, 5-fold, 10-fold, 20-fold, 50-fold, 100-fold, 200-fold, 500-fold, or 1000-fold that of the normal cell or animal.

According to one aspect of the invention, a polynucleotide encoding a dominant negative form of a mismatch repair protein is introduced into a cell. The gene can be any dominant negative allele encoding a protein that is part of a mismatch repair complex, for example, PMS2, PMS1, MLH1, or MSH2. The dominant negative allele can be naturally occurring or made in the laboratory. The polynucleotide can be in the form of genomic DNA, cDNA, RNA, or a chemically synthesized polynucleotide.

The polynucleotide can be cloned into an expression vector containing a constitutively active promoter segment (such as but not limited to CMV, SV40, Elongation Factor or LTR sequences) or to inducible promoter sequences such as the steroid inducible pIND vector (InVitrogen), where the expression of the dominant negative mismatch repair gene can be regulated. The polynucleotide can be introduced into the cell by transfection.

Transfection is any process whereby a polynucleotide is introduced into a cell. The process of transfection can be carried out in a living animal, e.g., using a vector for gene therapy, or it can be carried out in vitro, e.g., using a suspension of one or more isolated cells in culture. The cell can be any type of eukaryotic cell, including, for example, cells isolated from humans or other primates, mammals or other vertebrates, invertebrates, and single celled organisms such as protozoa, yeast, or bacteria.

In general, transfection will be carried out using a suspension of cells, or a single cell, but other methods can also be applied as long as a sufficient fraction of the treated cells or tissue incorporates the polynucleotide so as to allow transfected cells to be grown and utilized. The protein product of the polynucleotide may be transiently or stably expressed in the cell. Techniques for transfection are well known and available techniques for introducing polynucleotides include but are not limited to electroporation, transduction, cell fusion, the use of calcium chloride, and packaging of the polynucleotide together with lipid for fusion with the cells of interest. Once a cell has been transfected with the mismatch repair gene, the cell can be grown and reproduced in culture. If the transfection is stable, such that the gene is expressed at a consistent level for many cell generations, then a cell line results.

An isolated cell is a cell obtained from a tissue of humans or animals by mechanically separating out individual cells and transferring them to a suitable cell culture medium, either with or without pretreatment of the tissue with enzymes, e.g., collagenase or trypsin. Such isolated cells are typically cultured in the absence of other types of cells. Cells selected for the introduction of a dominant negative allele of a mismatch repair gene may be derived from a eukaryotic organism in the form of a primary cell culture or an immortalized cell line, or may be derived from suspensions of single-celled organisms.

The invention described herein is useful for creating microbial-resistant mammalian cells that secrete new antimicrobial biochemical agents, either protein or non-protein in nature. Furthermore, the invention can be applied to cell lines that express known antimicrobial agents as a means to enhance the biochemical activity of the antimicrobial agent.

Once a transfected cell line has been produced, it can be used to generate new mutations in one or more gene(s) of interest or in genes that have not been previously described. A gene of interest can be any gene naturally possessed by the cell line or introduced into the cell line by standard methods known in the art. An advantage of using transfected cells or to induce mutation(s) in a gene or genes of interest that encode antimicrobial activity is that the cell need not be exposed to mutagenic chemicals or radiation, which may have secondary harmful effects, both on the object of the exposure and on the workers. Furthermore, it has been demonstrated that chemical and physical mutagens are base pair specific in the way they alter the structure of DNA; the invention described herein results in mutations that are not dependent upon the specific nucleotide or a specific string of nucleotides and is a truly random genetic approach. Therefore, use of the present invention to obtain mutations in novel or known antimicrobial genes will be much more efficient and have a higher likelihood of success in contrast to conventional mutagenesis with chemical or irradiation. Once a new antimicrobial trait is identified in a sibling cell, the dominant negative allele can be removed from the cell by a variety of standard methods known in the art. For example, the gene can be directly knocked out the allele by technologies used by those skilled in the art or use of a inducible expression system; the dominant-negative allele is driven by a standard promoter that is regulated by inclusion of an inducer, withdrawal of the inducer results in attenuation of the expression of the dominant negative mismatch repair mutant and a normal DNA repair process will ensue.

New antimicrobial agents are selected from cells that have been exposed to the dominant negative mismatch repair process followed by incubating the mutant cells in the presence of the microbe for which an novel antimicrobial agent is sought. The novel antimicrobial agent is purified by standard methods known to those skilled in the art and characterized. The antimicrobial agents are re-screened to determine the specific activity of the novel antimicrobial as well as tested against a broad range of microbes to determine spectrum of activity. The gene(s) that encode the novel antimicrobial are isolated by standard well known methods to those in the art. The mutations can be detected by analyzing for alterations in the genotype of the cells by examining the sequence of genomic DNA, cDNA, messenger RNA, or amino acids associated with the gene of interest. A mutant polypeptide can be detected by identifying alterations in electrophoretic mobility, spectroscopic properties, or other physical or structural characteristics of a protein encoded by a mutant gene when the cell that has undergone alteration encodes a known antimicrobial that is altered by the means described in the current invention to obtain a more efficacious antimicrobial.

Examples of Mismatch Repair Proteins and Nucleic Acid Sequences Include the Following:

```
PMS2 (mouse)                                                              (SEQ ID NO:7)
MEQTEGVSTE CAKAIKPIDG KSVHQICSGQ VILSLSTAVK ELIENSVDAG ATTIDLRLKD   60

YGVDLIEVSD NGCGVEEENF EGLALKHHTS KIQEFADLTQ VETFGFRGEA LSSLCALSDV  120

TISTCHGSAS VGTRLVFDHN GKITQKTPYP RPKGTTVSVQ HLFYTLPVRY KEFQRNIKKE  180

YSKMVQVLQA YCIISAGVRV SCTNQLGQGK RHAVVCTSGT SGMKENIGSV FGQKQLQSLI  240

PFVQLPPSDA VCEEYGLSTS GRHKTFSTFR ASFHSARTAP GGVQQTGSFS SSIRGPVTQQ  300

RSLSLSMRFY HMYNRHQYPF VVLNVSVDSE CVDINVTPDK RQILLQEEKL LLAVLKTSLI  360

GMFDSDANKL NVNQQPLLDV EGNLVKLHTA ELEKPVPGKQ DNSPSLKSTA DEKRVASISR  420

LREAFSLHPT KEIKSRGPET AELTRSFPSE KRGVLSSYPS DVISYRGLRG SQDKLVSPTD  480

SPGDCMDREK IEKDSGLSST SAGSEEEFST PEVASSFSSD YNVSSLEDRP SQETINCGDL  540

DCRPPGTGQS LKPEDHGYQC KALPLARLSP TNAKRFKTEE RPSNVNISQR LPGPQSTSAA  600

EVDVAIKMNK RIVLLEFSLS SLAKRMKQLQ HLKAQNKHEL SYRKFRAKIC PGENQAAEDE  660

LRKEISKSMF AEMEILGQFN LGFIVTKLKE DLFLVDQHAA DEKYNFEMLQ QHTVLQAQRL  720

ITPQTLNLTA VNEAVLIENL EIFRKNGFDF VIDEDAPVTE RAKLISLPTS KNWTFGPQDI  780

DELIFMLSDS PGVMCRPSRV RQMFASRACR KSVMIGTALN ASEMKKLITH MGEMDHPWNC  840
```

-continued

PHGRPTMRHV ANLDVISQN                                                    859

PMS2 (mouse cDNA)                                                       (SEQ ID NO:8)

gaattccggt gaaggtcctg aagaatttcc agattcctga gtatcattgg aggagacaga        60
taacctgtcg tcaggtaacg atggtgtata tgcaacagaa atgggtgttc ctggagacgc       120
gtcttttccc gagagcggca ccgcaactct cccgcggtga ctgtgactgg aggagtcctg       180
catccatgga gcaaaccgaa ggcgtgagta cagaatgtgc taaggccatc aagcctattg       240
atgggaagtc agtccatcaa atttgttctg gcaggtgat actcagttta agcaccgctg        300
tgaaggagtt gatagaaaat agtgtagatg ctggtgctac tactattgat ctaaggctta      360
aagactatgg ggtggacctc attgaagttt cagacaatgg atgtggggta gaagaagaaa      420
actttgaagg tctagctctg aaacatcaca catctaagat tcaagagttt gccgacctca      480
cgcaggttga aactttcggc tttcgggggg aagctctgag ctctctgtgt gcactaagtg      540
atgtcactat atctacctgc cacggtctg caagcgttgg gactcgactg gtgtttgacc        600
ataatgggaa atcacccag aaaactccct acccccgacc taaggaacc acagtcagtg         660 tgcagcactt atttataca ctacccgtgc gttacaaaga gtttcagagg aacattaaaa        720
aggagtattc caaaatggtg caggtcttac aggcgtactg tatcatctca gcaggcgtcc      780
gtgtaagctg cactaatcag ctcggacagg ggaagcggca cgctgtggtg tgcacaagcg      840
gcacgtctgg catgaaggaa atatcgggt ctgtgtttgg ccagaagcag ttgcaaagcc        900
tcattccttt tgttcagctg cccctagta cgctgtgtg tgaagagtac ggcctgagca        960
cttcaggacg ccacaaaacc ttttctacgt ttcgggcttc atttcacagt gcacgcacgg      1020 cgccggagg agtgcaacag acaggcagtt tttcttcatc aatcagaggc cctgtgaccc       1080
agcaaaggtc tctaagcttg tcaatgaggt tttatcacat gtataaccgg catcagtacc      1140
catttgtcgt ccttaacgtt tccgttgact cagaatgtgt ggatattaat gtaactccag      1200
ataaaaggca aattctacta caagaagaga agctattgct ggccgtttta aagacctcct      1260
tgataggaat gttgacagt gatgcaaaca agcttaatgt caaccagcag ccactgctag       1320
atgttgaagg taacttagta aagctgcata ctgcagaact agaaaagcct gtgccaggaa      1380
agcaagataa ctctccttca ctgaagagca cagcagacga gaaagggta gcatccatct       1440 ccaggctgag agaggccttt tctcttcatc ctactaaaga gatcaagtct aggggtccaa      1500
agactgctga actgacacgg agttttccaa gtgagaaaag gggcgtgtta tcctcttatc      1560 cttcagacg catctcttac agaggcctcc gtggctcgca ggacaaattg gtgagtccca       1620
cggacagccc tggtgactgt atggacagag agaaaataga aaaagactca gggctcagca     1680
gcacctcagc tggctctgag gaagagttca gcacccccaga agtggccagt agctttagca     1740
gtgactataa cgtgagctcc ctagaagaca gaccttctca ggaaaccata aactgtggtg      1800
acctggactg ccgtcctcca ggtacaggac agtccttgaa gccagaagac catggatatc     1860
aatgcaaagc tctacctcta gctcgtctgt cacccacaaa tgccaagcgc ttcaagacag      1920
aggaaagacc ctcaaatgtc aacatttctc aaagattgcc tggtcctcag agcacctcag    1980
cagctgaggt cgatgtagcc ataaaaatga ataagagaat cgtgctcctc gagttctctc     2040
tgagttctct agctaagcga atgaagcagt tacagcacct aaaggcgcag aacaaacatg     2100
aactgagtta cagaaaattt agggccaaga tttgccctgg agaaaaccaa gcagcagaag      2160
atgaactcag aaaagagatt agtaaatcga tgtttcaga gatggagatc ttgggtcagt       2220
ttaacctggg atttatagta accaaactga agaggacct cttcctggtg gaccagcatg       2280

-continued

```
ctgcggatga gaagtacaac tttgagatgc tgcagcagca cacggtgctc caggcgcaga   2340
ggctcatcac accccagact ctgaacttaa ctgctgtcaa tgaagctgta ctgatagaaa   2400
atctggaaat attcagaaag aatggctttg actttgtcat tgatgaggat gctccagtca   2460
ctgaaagggc taaattgatt tccttaccaa ctagtaaaaa ctggaccttt ggaccccaag   2520
atatagatga actgatcttt atgttaagtg acagccctgg ggtcatgtgc cggccctcac   2580
gagtcagaca gatgtttgct tccagagcct gtcggaagtc agtgatgatt ggaacggcgc   2640
tcaatgcgag cgagatgaag aagctcatca cccacatggg tgagatggac caccccctgga  2700
actgccccca cggcaggcca accatgaggc acgttgccaa tctggatgtc atctctcaga   2760
actgacacac cccttgtagc atagagtttta ttacagattg ttcggtttgc aaagagaagg  2820
ttttaagtaa tctgattatc gttgtacaaa aattagcatg ctgctttaat gtactggatc   2880
catttaaaag cagtgttaag gcaggcatga tggagtgttc ctctagctca gctacttggg   2940
tgatccggtg ggagctcatg tgagcccagg actttgagac cactccgagc acattcatg   3000
agactcaatt caaggacaaa aaaaaaaaga tattttgaa gccttttaaa aaaaaa        3056
```

PMS2 (human)                                                       (SEQ ID NO:9)
```
MERAESSSTE PAKAIKPIDR KSVHQICSGQ VVLSLSTAVK ELVENSLDAG ATNIDLKLKD    60
YGVDLIEVSD NGCGVEEENF EGLTLKHHTS KIQEFADLTQ VETFGFRGEA LSSLCALSDV  120
TISTCHASAK VGTRLMFDHN GKIIQKTPYP RPRGTTVSVQ QLFSTLPVRH KEFQRNIKKE  180
YAKMVQVLHA YCIISAGIRV SCTNQLGQGK RQPVVCTGGS PSIKENIGSV FGQKQLQSLI  240
PFVQLPPSDS VCEEYGLSCS DALHNLFYIS GFISQCTHGV GRSSTDRQFF FINRRPCDPA  300
KVCRLVNEVY HMYNRHQYPF VVLNISVDSE CVDINVTPDK RQILLQEEKL LLAVLKTSLI  360
GMFDSDVNKL NVSQQPLLDV EGNLIKMHAA DLEKPMVEKQ DQSPSLRTGE EKKDVSISRL  420
REAFSLRHTT ENKPHSPKTP EPRRSPLGQK RGMLSSSTSG AISDKGVLRP QKEAVSSSHG  480
PSDPTDRAEV EKDSGHGSTS VDSEGFSIPD TGSHCSSEYA ASSPGDRGSQ EHVDSQEKAP  540
ETDDSFSDVD CHSNQEDTGC KFRVLPQPTN LATPNTKRFK KEEILSSSDI CQKLVNTQDM  600
SASQVDVAVK INKKVVPLDF SMSSLAKRIK QLHHFAQQSE GEQNYRKFRA KICPGENQAA  660
EDELRKEISK TMFAEMEIIG QFNLGFIITK LNEDIFIVDQ HATDEKYNFE MLQQHTVLQG  720
QRLIAPQTLN LTAVNEAVLI ENLEIFRKNG FDFVIDENAP VTERAKLISL PTSKNWTFGP  780
QDVDELIFML SDSPGVMCRP SRVKQMFASR ACRKSVMIGT ALNTSEMKKL ITHMGEMDHP  840
WNCPHGRPTM RHIANLGVIS QN                                           862
```

PMS2 (human cDNA)                                                  (SEQ ID NO:10)
```
cgaggcggat cgggtgttgc atccatggag cgagctgaga gctcgagtac agaacctgct    60
aaggccatca aacctattga tcggaagtca gtccatcaga tttgctctgg gcaggtggta   120
ctgagtctaa gcactgcggt aaaggagtta gtagaaaaca gtctggatgc tggtgccact   180
aatattgatc taaagcttaa ggactatgga gtggatctta ttgaagtttc agacaatgga   240
tgtggggtag aagaagaaaa cttcgaaggc ttaactctga acatcacac atctaagatt   300
caagagtttg ccgacctaac tcaggttgaa acttttggct tcgggggga agctctgagc   360
tcactttgtg cactgagcga tgtcaccatt tctacctgcc acgcatcggc gaaggttgga   420
actcgactga tgtttgatca caatgggaaa attatccaga aaccccccta cccccgcccc   480
agagggacca cagtcagcgt gcagcagtta ttttccacac tacctgtgcg ccataaggaa   540
tttcaaagga atattaagaa ggagtatgcc aaaatggtcc aggtcttaca tgcatactgt   600
atcatttcag caggcatccg tgtaagttgc accaatcagc ttggacaagg aaaacgacag   660
```

-continued

```
cctgtggtat gcacaggtgg aagccccagc ataaaggaaa atatcggctc tgtgtttggg    720
cagaagcagt tgcaaagcct cattcctttt gttcagctgc ccctagtga ctccgtgtgt     780 gaagagtacg gtttgagctg ttcggatgct ctgcataatc ttttttacat ctcaggtttc    840
atttcacaat gcacgcatgg agttggaagg agttcaacag acagacagtt tttctttatc    900
aaccggcggc cttgtgaccc agcaaaggtc tgcagactcg tgaatgaggt ctaccacatg    960
tataatcgac accagtatcc atttgttgtt cttaacattt ctgttgattc agaatgcgtt   1020
gatatcaatg ttactccaga taaaaggcaa attttgctac aagaggaaaa gcttttgttg   1080
gcagttttaa agacctcttt gataggaatg tttgatagtg atgtcaacaa gctaaatgtc   1140
agtcagcagc cactgctgga tgttgaaggt aacttaataa aaatgcatgc agcggatttg   1200
gaaaagccca tggtagaaaa gcaggatcaa tccccttcat taaggactgg agaagaaaaa   1260
aaagacgtgt ccatttccag actgcgagag gccttttctc ttcgtcacac aacagagaac   1320
aagcctcaca gcccaaagac tccagaacca gaaggagcc ctctaggaca gaaaagggt    1380 atgctgtctt ctagcacttc aggtgccatc tctgacaaag gcgtcctgag acctcagaaa   1440
gaggcagtga gttccagtca cggacccagc gaccctacgg acagagcgga ggtggagaag   1500
gactcggggc acggcagcac ttccgtggat tctgaggggt tcagcatccc agacacgggc   1560
agtcactgca gcagcgagta tgcggccagc tccccagggg acaggggctc gcaggaacat   1620
gtggactctc aggagaaagc gcctgaaact gacgactctt tttcagatgt ggactgccat   1680
tcaaaccagg aagataccgg atgtaaattt cgagttttgc ctcagccaac taatctcgca   1740
accccaaaca caaagcgttt taaaaagaa gaaattcttt ccagttctga catttgtcaa    1800
aagttagtaa atactcagga catgtcagcc tctcaggttg atgtagctgt gaaaattaat   1860
aagaaagttg tgcccctgga cttttctatg agttctttag ctaaacgaat aaagcagtta   1920
catcatgaag cacagcaaag tgaaggggaa cagaattaca ggaagtttag ggcaaagatt   1980
tgtcctggag aaaatcaagc agccgaagat gaactaagaa aagagataag taaaacgatg   2040
tttgcagaaa tggaaatcat tggtcagttt aacctgggat ttataataac caaactgaat   2100
gaggatatct tcatagtgga ccagcatgcc acggacgaga gtataacttc gagatgctg    2160 cagcagcaca ccgtgctcca ggggcagagg ctcatagcac ctcagactct caacttaact   2220
gctgttaatg aagctgttct gatagaaaat ctggaaatat ttagaaagaa tggctttgat   2280
tttgttatcg atgaaaatgc tccagtcact gaaagggcta actgatttc cttgccaact    2340 agtaaaaact ggaccttcgg accccaggac gtcgatgaac tgatcttcat gctgagcgac   2400
agccctgggg tcatgtgccg gccttcccga gtcaagcaga tgtttgcctc cagagcctgc   2460
cggaagtcgg tgatgattgg gactgctctt aacacaagcg agatgaagaa actgatcacc   2520
cacatggggg agatggacca cccctggaac tgtccccatg gaaggccaac catgagacac   2580
atcgccaacc tgggtgtcat ttctcagaac tgaccgtagt cactgtatgg aataattggt   2640
tttatcgcag attttatgt tttgaaagac agagtcttca ctaaccttt tgttttaaa      2700 atgaaacctg ctactaaaaa aaatacaca tcacacccat ttaaaagtga tcttgagaac    2760
cttttcaaac c                                                        2771
```

PMS1 (human)                                                        (SEQ ID NO:11)
MKQLPAATVR LLSSSQIITS VVSVVKELIE NSLDAGATSV DVKLENYGFD KIEVRDNGEG    60

IKAVDAPVMA MKYYTSKINS HEDLENLTTY GFRGEALGSI CCIAEVLITT RTAADNFSTQ   120

YVLDGSGHIL SQKPSHLGQG TTVTALRLFK NLPVRKQFYS TAKKCKDEIK KIQDLLMSFG   180

ILKPDLRIVF VHNKAVIWQK SRVSDHKMAL MSVLGTAVMN NMESFQYHSE ESQIYLSGFL   240

-continued

```
PKCDADHSFT SLSTPERSFI FINSRPVHQK DILKLIRHHY NLKCLKESTR LYPVFFLKID    300
VPTADVDVNL TPDKSQVLLQ NKESVLIALE NLMTTCYGPL PSTNSYENNK TDVSAADIVL    360
SKTAETDVLF NKVESSGKNY SNVDTSVIPF QNDMHNDESG KNTDDCLNHQ ISIGDFGYGH    420
CSSEISNIDK NTKNAFQDIS MSNVSWENSQ TEYSKTCFIS SVKHTQSENG NKDHIDESGE    480
NEEEAGLENS SEISADEWSR GNILKNSVGE NIEPVKILVP EKSLPCKVSN NNYPIPEQMN    540
LNEDSCNKKS NVIDNKSGKV TAYDLLSNRV IKKPMSASAL FVQDHRPQFL IENPKTSLED    600
ATLQIEELWK TLSEEEKLKY EEKATKDLER YNSQMKRAIE QESQMSLKDG RKKIKPTSAW    660
NLAQKHKLKT SLSNQPKLDE LLQSQIEKRR SQNIKMVQIP FSMKNLKINF KKQNKVDLEE    720
KDEPCLIHNL RFPDAWLMTS KTEVMLLNPY RVEEALLFKR LLENHKLPAE PLEKPIMLTE    780
SLFNGSHYLD VLYKMTADDQ RYSGSTYLSD PRLTANGFKI KLIPGVSITE NYLEIEGMAN    840
CLPFYGVADL KEILNAILNR NAKEVYECRP RKVISYLEGE AVRLSRQLPM YLSKEDIQDI    900
IYRMKHQFGN EIKECVHGRP FFHHLTYLPE TT                                 932
PMS1 (human)                                                    (SEQ ID NO:12)
ggcacgagtg gctgcttgcg gctagtggat ggtaattgcc tgcctcgcgc tagcagcaag     60
ctgctctgtt aaaagcgaaa atgaaacaat tgcctgcggc aacagttcga ctcctttcaa    120
gttctcagat catcacttcg gtggtcagtg ttgtaaaaga gcttattgaa aactccttgg    180
atgctggtgc cacaagcgta gatgttaaac tggagaacta tggatttgat aaaattgagg    240
tgcgagataa cggggagggt atcaaggctg ttgatgcacc tgtaatgca atgaagtact     300
acaccctcaaa ataaatagt catgaagatc ttgaaaattt gacaacttac ggttttcgtg    360
gagaagcctt gggtcaatt tgttgtatag ctgaggtttt aattacaaca gaacggctg      420
ctgataattt tagcacccag tatgttttag atggcagtgg ccacatactt tctcagaaac    480
cttcacatct tggtcaaggt acaactgtaa ctgctttaag attatttaag aatctacctg    540
taagaaagca gttttactca actgcaaaaa aatgtaaaga tgaaataaaa aagatccaag    600
atctcctcat gagctttggt atccttaaac ctgacttaag gattgtcttt gtacataaca    660
aggcagttat ttggcagaaa agcagagtat cagatcacaa gatggctctc atgtcagttc    720
tggggactgc tgttatgaac aatatggaat cctttcagta ccactctgaa gaatctcaga    780
tttatctcag tggatttctt ccaaagtgtg atgcagacca ctctttcact agtctttcaa    840
caccagaaag aagtttcatc ttcataaaca gtcgaccagt acatcaaaaa gatatcttaa    900
agttaatccg acatcattac aatctgaaat gcctaaagga atctactcgt ttgtatcctg    960
ttttctttct gaaaatcgat gttcctacag ctgatgttga tgtaaattta acaccagata   1020
aaagccaagt attattacaa aataaggaat ctgtttttaat tgctcttgaa aatctgatga   1080
cgacttgtta tggaccatta cctagtacaa attcttatga aaataataaa acagatgttt   1140
ccgcagctga catcgttctt agtaaaacag cagaaacaga tgtgcttttt aataaagtgg   1200
aatcatctgg aaagaattat tcaaatgttg atacttcagt cattccattc caaaatgata   1260
tgcataatga tgaatctgga aaaaacactg atgattgttt aaatcaccag ataagtattg   1320
gtgactttgg ttatggtcat tgtagtagtg aaatttctaa cattgataaa aacactaaga   1380
atgcatttca ggacatttca atgagtaatg tatcatggga gaactctcag acggaatata   1440
gtaaaacttg ttttataagt tccgttaagc acacccagtc agaaaatggc aataaagacc   1500
atatagatga gagtgggaa aatgaggaag aagcaggtct tgaaaactct tcggaaattt   1560
ctgcagatga gtggagcagg ggaaatatac ttaaaaattc agtgggagag aatattgaac   1620
```

-continued

```
ctgtgaaaat tttagtgcct gaaaaaagtt taccatgtaa agtaagtaat aataattatc  1680
caatccctga acaaatgaat cttaatgaag attcatgtaa caaaaaatca aatgtaatag  1740
ataataaatc tggaaaagtt acagcttatg atttacttag caatcgagta atcaagaaac  1800
ccatgtcagc aagtgctctt tttgttcaag atcatcgtcc tcagtttctc atagaaaatc  1860
ctaagactag tttagaggat gcaacactac aaattgaaga actgtggaag acattgagtg  1920
aagaggaaaa actgaaatat gaagagaagg ctactaaaga cttggaacga tacaatagtc  1980
aaatgaagag agccattgaa caggagtcac aaatgtcact aaaagatggc agaaaaaaga  2040
taaaacccac cagcgcatgg aatttggccc agaagcacaa gttaaaaacc tcattatcta  2100
atcaaccaaa acttgatgaa ctccttcagt cccaaattga aaaagaagg agtcaaaata  2160
ttaaaatggt acagatcccc ttttctatga aaaacttaaa aataaatttt aagaaacaaa  2220
acaaagttga cttagaagag aaggatgaac cttgcttgat ccacaatctc aggtttcctg  2280
atgcatggct aatgacatcc aaaacagagg taatgttatt aaatccatat agagtagaag  2340
aagccctgct atttaaaaga cttcttgaga atcataaact tcctgcagag ccactggaaa  2400
agccaattat gttaacagag agtctttta atggatctca ttatttagac gttttatata  2460
aaatgacagc agatgaccaa agatacagtg gatcaactta cctgtctgat cctcgtctta  2520
cagcgaatgg tttcaagata aaattgatac caggagtttc aattactgaa aattacttgg  2580
aaatagaagg aatggctaat tgtctcccat tctatggagt agcagattta aaagaaattc  2640
ttaatgctat attaaacaga aatgcaaagg aagtttatga atgtagacct cgcaaagtga  2700
taagttattt agagggagaa gcagtgcgtc tatccagaca attacccatg tacttatcaa  2760
aagaggacat ccaagacatt atctacagaa tgaagcacca gtttggaaat gaattaaag  2820
agtgtgttca tggtcgccca ttttttcatc atttaaccta tcttccagaa actacatgat  2880
taaatatgtt taagaagatt agttaccatt gaaattggtt ctgtcataaa acagcatgag  2940
tctggtttta aattatcttt gtattatgtg tcacatggtt atttttaaa tgaggattca  3000
ctgacttgtt tttatattga aaaagttcc acgtattgta gaaacgtaa ataaactaat  3060
aac                                                                3063
```

```
MSH2 (human)                                                    (SEQ ID NO:13)
MAVQPKETLQ LESAAEVGFV RFFQGMPEKP TTTVRLFDRG DFYTAHGEDA LLAAREVFKT   60
QGVIKYMGPA GAKNLQSVVL SKMNFESFVK DLLLVRQYRV EVYKNRAGNK ASKENDWYLA  120
YKASPGNLSQ FEDILFGNND MSASIGVVGV KMSAVDGQRQ VGVGYVDSIQ RKLGLCEFPD  180
NDQFSNLEAL LIQIGPKECV LPGGETAGDM GKLRQIIQRG GILITERKKA DFSTKDIYQD  240
LNRLLKGKKG EQMNSAVLPE MENQVAVSSL SAVIKFLELL SDDSNFGQFE LTTFDFSQYM  300
KLDIAAVRAL NLFQGSVEDT TGSQSLAALL NKCKTPQGQR LVNQWIKQPL MDKNRIEERL  360
NLVEAFVEDA ELRQTLQEDL LRRFPDLNRL AKKFQRQAAN LQDCYRLYQG INQLPNVIQA  420
LEKHEGKHQK LLLAVFVTPL TDLRSDFSKF QEMIETTLDM DQVENHEFLV KPSFDPNLSE  480
LREIMNDLEK KMQSTLISAA RDLGLDPGKQ IKLDSSAQFG YYFRVTCKEE KVLRNNKNFS  540
TVDIQKNGVK FTNSKLTSLN EEYTKNKTEY EEAQDAIVKE IVNISSGYVE PMQTLNDVLA  600
QLDAVVSFAH VSNGAPVPYV RPAILEKGQG RIILKASRHA CVEVQDEIAF IPNDVYFEKD  660
KQMFHIITGP NMGGKSTYIR QTGVIVLMAQ IGCFVPCESA EVSIVDCILA RVGAGDSQLK  720
GVSTFMAEML ETASILRSAT KDSLIIIDEL GRGTSTYDGF GLAWAISEYI ATKIGAFCMF  780
ATHFHELTAL ANQIPTVNNL HVTALTTEET LTMLYQVKKG VCDQSFGIHV AELANFPKHV  840
IECAKQKALE LEEFQYIGES QGYDIMEPAA KKCYLEREQG EKIIQEFLSK VKQMPFTEMS  900
```

-continued

EENITIKLKQ LKAEVIAKNN SFVNEIISRI KVTT                934

MSH2 (human cDNA)                                   (SEQ ID NO:14)

```
ggcgggaaac agcttagtgg gtgtggggtc gcgcattttc ttcaaccagg aggtgaggag   60
gtttcgacat ggcggtgcag ccgaaggaga cgctgcagtt ggagagcgcg gccgaggtcg  120
gcttcgtgcg cttctttcag ggcatgccgg agaagccgac caccacagtg cgcctcttcg  180
accgggcga cttctatacg gcgcacggcg aggacgcgct gctggccgcc cgggaggtgt  240
tcaagaccca gggggtgatc aagtacatgg ggccggcagg agcaaagaat ctgcagagtg  300
ttgtgcttag taaaatgaat tttgaatctt ttgtaaaaga tcttcttctg gttcgccagt  360
atagagttga agtttataag aatagagctg aaataaggc atccaaggag aatgattggt  420
atttggcata taaggcttct cctggcaatc tctctcagtt tgaagacatt ctctttggta  480
acaatgatat gtcagcttcc attggtgttg tgggtgttaa aatgtccgca gttgatggcc  540
agagacaggt tggagttggg tatgtggatt ccatacagag gaaactagga ctgtgtgaat  600
tccctgataa tgatcagttc tccaatcttg aggctctcct catccagatt ggaccaaagg  660
aatgtgtttt acccggagga gagactgctg agacatggg gaaactgaga cagataattc  720
aaagaggagg aattctgatc acagaaagaa aaaagctga cttttccaca aagacattt   780
atcaggacct caaccggttg ttgaaaggca aaaagggaga gcagatgaat agtgctgtat  840
tgccagaaat ggagaatcag gttgcagttt catcactgtc tgcggtaatc aagttttag  900
aactcttatc agatgattcc aactttggac agtttgaact gactactttt gacttcagcc  960
agtatatgaa attggatatt gcagcagtca gagcccttaa ccttttttcag ggttctgttg 1020
aagataccac tggctctcag tctctggctg ccttgctgaa taagtgtaaa accctcaag  1080
gacaaagact tgttaaccag tggattaagc agcctctcat ggataagaac agaatagagg 1140
agagattgaa tttagtggaa gcttttgtag aagatgcaga attgaggcag actttacaag 1200
aagatttact tcgtcgattc ccagatctta accgacttgc caagaagttt caaagacaag 1260
cagcaaactt acaagattgt taccgactct atcagggtat aaatcaacta cctaatgtta 1320
tacaggctct ggaaaaacat gaaggaaaac accagaaatt attgttggca gttttttgtga 1380
ctcctcttac tgatcttcgt tctgacttct ccaagtttca ggaaatgata gaaacaactt 1440
tagatatgga tcaggtggaa aaccatgaat tccttgtaaa accttcattt gatcctaatc 1500
tcagtgaatt aagagaaata atgaatgact ggaaaagaa gatgcagtca acattaataa 1560
gtgcagccag atcttggc ttggaccctg gcaaacagat taaactggat tccagtgcac 1620
agtttggata ttactttcgt gtaacctgta aggaagaaaa agtccttcgt aacaataaaa 1680
actttagtac tgtagatatc cagaagaatg gtgttaaatt taccaacagc aaattgactt 1740
ctttaaatga agagtatacc aaaaataaaa cagaatatga agaagccag gatgccattg 1800
ttaaagaaat tgtcaatatt tcttcaggct atgtagaacc aatgcagaca ctcaatgatg 1860
tgttagctca gctagatgct gttgtcagct tgctcacgt gtcaaatgga gcacctgttc 1920
catatgtacg accagccatt ttggagaaag acaaggaag aattatatta aaagcatcca 1980
ggcatgcttg tgttgaagtt caagatgaaa ttgcatttat cctaatgac gtatactttg 2040
aaaaagataa acagatgttc cacatcatta ctggcccaa tatgggaggt aaatcaacat 2100
atattcgaca aactgggtg atagtactca tggcccaaat tgggtgtttt gtgccatgtg 2160
agtcagcaga agtgtccatt gtggactgca ctcttagccc gtagggggct ggtgacagtc 2220
aattgaaagg agtctccacg ttcatggctg aaatgttgga aactgcttct atcctcaggt 2280
```

-continued

```
ctgcaaccaa agattcatta ataatcatag atgaattggg aagaggaact tctacctacg    2340
atggatttgg gttagcatgg gctatatcag aatacattgc aacaaagatt ggtgcttttt    2400
gcatgtttgc aacccatttt catgaactta ctgccttggc caatcagata ccaactgtta    2460
ataatctaca tgtcacagca ctcaccactg aagagaccct aactatgctt tatcaggtga    2520
agaaaggtgt ctgtgatcaa agttttggga ttcatgttgc agagcttgct aatttcccta    2580
agcatgtaat agagtgtgct aaacagaaag ccctggaact tgaggagttt cagtatattg    2640
gagaatcgca aggatatgat atcatggaac cagcagcaaa gaagtgctat ctggaaagag    2700
agcaaggtga aaaattatt caggagttcc tgtccaaggt gaaacaaatg ccctttactg    2760
aaatgtcaga agaaacatc acaataaagt taaaacagct aaaagctgaa gtaatagcaa    2820
agaataatag ctttgtaaat gaatcattt cacgaataaa agttactacg tgaaaaatcc    2880
cagtaatgga atgaaggtaa tattgataag ctattgtctg taatagtttt atattgtttt    2940 atattaccc ttttccata gtgttaactg tcagtgccca tgggctatca acttaataag    3000
atatttagta atattttact ttgaggacat tttcaaagat tttatttttg aaaaatgaga    3060
gctgtaactg aggactgttt gcaattgaca taggcaataa taagtgatgt gctgaatttt    3120
ataaataaaa tcatgtagtt tgtgg                                           3145
```

MLH1 (human)                                                          (SEQ ID NO:15)
```
MSFVAGVIRR LDETVVNRIA AGEVIQRPAN AIKEMIENCL DAKSTSIQVI VKEGGLKLIQ     60

IQDNGTGIRK EDLDIVCERF TTSKLQSFED LASISTYGFR GEALASISHV AHVTITTKTA    120

DGKCAYRASY SDGKLKAPPK PCAGNQGTQI TVEDLFYNIA TRRKALKNPS EEYGKILEVV    180

GRYSVHNAGI SFSVKKQGET VADVRTLPNA STVDNIRSIF GNAVSRELIE IGCEDKTLAF    240

KMNGYISNAN YSVKKCIFLL FINHRLVEST SLRKAIETVY AAYLPKNTHP FLYLSLEISP    300

QNVDVNVHPT KHEVHFLHEE SILERVQQHI ESKLLGSNSS RMYFTQTLLP GLAGPSGEMV    360

KSTTSLTSSS TSGSSDKVYA HQMVRTDSRE QKLDAFLQPL SKPLSSQPQA IVTEDKTDIS    420

SGRARQQDEE MLELPAPAEV AAKNQSLEGD TTKGTSEMSE KRGPTSSNPR KRHREDSDVE    480

MVEDDSRKEM TAACTPRRRI INLTSVLSLQ EEINEQGHEV LREMLHNHSF VGCVNPQWAL    540

AQHQTKLYLL NTTKLSEELF YQILIYDFAN FGVLRLSEPA PLFDLAMLAL DSPESGWTEE    600

DGPKEGLAEY IVEFLKKKAE MLADYFSLEI DEEGNLIGLP LLIDNYVPPL EGLPIFILRL    660

ATEVNWDEEK ECFESLSKEC AMFYSIRKQY ISEESTLSGQ QSEVPGSIPN SWKWTVEHIV    720

YKALRSHILP PKHFTEDGNI LQLANLPDLY KVFERC                              756
```

MLH1 (human)                                                          (SEQ ID NO:16)
```
cttggctctt ctggcgccaa aatgtcgttc gtggcagggg ttattcggcg gctggacgag     60
acagtggtga accgcatcgc ggcgggggaa gttatccagc ggccagctaa tgctatcaaa    120
gagatgattg agaactgttt agatgcaaaa tccacaagta ttcaagtgat tgttaaagag    180
ggaggcctga gttgattca gatccaagac aatggcaccg ggatcaggaa agaagatctg    240
gatattgtat gtgaaaggtt cactactagt aaactgcagt cctttgagga tttagccagt    300
atttctacct atggctttcg aggtgaggct ttggccagca taagccatgt ggctcatgtt    360
actattacaa cgaaaacagc tgatggaaag tgtgcataca gagcaagtta ctcagatgga    420
aaactgaaag cccctcctaa accatgtgct ggcaatcaag ggacccagat tacggtggag    480
gacctttttt acaacatagc cacgaggaga aaagctttaa aaaatccaag tgaagaatat    540
gggaaaattt tggaagttgt tggcaggtat tcagtacaca atgcaggcat tagtttctca    600
gttaaaaaac aaggagagac agtagctgat gttaggacac tacccaatgc ctcaaccgtg    660
```

-continued

```
gacaatattc gctccatctt tggaaatgct gttagtcgag aactgataga aattggatgt    720
gaggataaaa ccctagcctt caaaatgaat ggttacatat ccaatgcaaa ctactcagtg    780
aagaagtgca tcttcttact cttcatcaac catcgtctgg tagaatcaac ttccttgaga    840
aaagccatag aaacagtgta tgcagcctat tgcccaaaa acacacaccc attcctgtac     900
ctcagtttag aaatcagtcc ccagaatgtg gatgttaatg tgcaccccac aaagcatgaa    960
gttcacttcc tgcacgagga gagcatcctg gagcgggtgc agcagcacat cgagagcaag   1020
ctcctgggct ccaattcctc caggatgtac ttcacccaga ctttgctacc aggacttgct   1080
ggcccctctg gggagatggt taaatccaca acaagtctga cctcgtcttc tacttctgga   1140
agtagtgata aggtctatgc ccaccagatg gttcgtacag attcccggga acagaagctt   1200
gatgcatttc tgcagcctct gagcaaaccc ctgtccagtc agcccaggc cattgtcaca    1260 gaggataaga cagatatttc tagtggcagg gctaggcagc aagatgagga gatgcttgaa   1320
ctcccagccc ctgctgaagt ggctgccaaa aatcagagct ggaggggga tacaacaaag    1380 gggacttcag aaatgtcaga agagagga cctacttcca gcaaccccag aaagagacat     1440
cgggaagatt ctgatgtgga aatggtggaa gatgattccc gaaaggaaat gactgcagct   1500
tgtacccccc ggagaaggat cattaacctc actagtgttt tgagtctcca ggaagaaatt   1560
aatgagcagg gacatgaggt tctccgggag atgttgcata ccactccctt cgtgggctgt   1620
gtgaatcctc agtgggcctt ggcacagcat caaaccaagt tataccttct caacaccacc   1680
aagcttagtg aagaactgtt ctaccagata ctcatttatg attttgccaa ttttggtgtt   1740
ctcaggttat cggagccagc accgctcttt gaccttgcca tgcttgcctt agatagtcca   1800
gagagtggct ggacagagga agatggtccc aaagaaggac ttgctgaata cattgttgag   1860
tttctgaaga gaaggctga gatgcttgca gactatttct ctttggaaat tgatgaggaa    1920
gggaacctga ttggattacc ccttctgatt gacaactatg tgccccttt ggagggactg    1980 cctatcttca ttcttcgact agccactgag gtgaattggg acgaagaaaa ggaatgtttt   2040
gaaagcctca gtaaagaatg cgctatgttc tattccatcc ggaagcagta catatctgag   2100
gagtcgaccc tctcaggcca gcagagtgaa gtgcctggct ccattccaaa ctcctggaag   2160
tggactgtgg aacacattgt ctataaagcc ttgcgctcac acattctgcc tcctaaacat   2220
ttcacagaag atgaaatat cctgcagctt gctaacctgc ctgatctata caaagtcttt    2280
gagaggtgtt aaatatggtt atttatgcac tgtgggatgt gttcttcttt ctctgtattc   2340
cgatacaaag tgttgtatca aagtgtgata tacaaagtgt accaacataa gtgttggtag   2400
cacttaagac ttatacttgc cttctgatag tattccttta tacacagtgg attgattata   2460
aataaataga tgtgtcttaa cata                                          2484
``` hPMS2-134 (human) (SEQ ID NO:17)
```
MERAESSSTE PAKAIKPIDR KSVHQICSGQ VVLSLSTAVK ELVENSLDAG ATNIDLKLKD   60

YGVDLIEVSD NCGVEEENF EGLTLKHHTS KIQEFADLTQ VETFGFRGEA LSSLCALSDV   120

TISTCHASAK VGT                                                     133
``` hPMS2-134 (human cDNA) (SEQ ID NO:18)
```
cgaggcggat cgggtgttgc atccatggag cgagctgaga gctcgagtac agaacctgct    60
aaggccatca aacctattga tcggaagtca gtccatcaga tttgctctgg gcaggtggta   120
ctgagtctaa gcactgcggt aaaggagtta gtagaaaaca gtctggatgc tggtgccact   180
aatattgatc taaagcttaa ggactatgga gtggatctta ttgaagtttc agacaatgga   240
tgtggggtag aagaagaaaa cttcgaaggc ttaactctga acatcacac atctaagatt    300
```

```
-continued
caagagtttg ccgacctaac tcaggttgaa acttttggct ttcggggga  agctctgagc    360 tcactttgtg cactgagcga tgtcaccatt tctacctgcc acgcatcggc gaaggttgga    420
acttga                                                               426
```

The above disclosure generally describes the present invention. A more complete understanding can be obtained by reference to the following specific examples, which are provided herein for purposes of illustration only, and are not intended to limit the scope of the invention.

EXAMPLES

Example 1 hPMS2-134 Encodes a Dominant Negative Mismatch Repair Protein

A profound defect in MMR was found in the normal cells of two HNPCC patients. That this defect was operative in vivo was demonstrated by the widespread presence of microsatellite instability in non neoplastic cells of such patients. One of the two patients had a germ line truncating mutation of the hPMS2 gene at codon 134 (the hPMS2 134 mutation), while the other patient had a small germ line deletion within the hMLH1 gene. Leach et al., Cell, 1993, 75, 1215 1225. These data contradicted the two hit model generally believed to explain the biochemical and biological features of HNPCC patients. The basis for this MMR deficiency in the normal cells of these patients was unclear, and several potential explanations were offered. For example, it was possible that the second allele of the relevant MMR gene was inactivated in the germ line of these patients through an undiscovered mechanism, or that unknown mutations of other genes involved in the MMR process were present that cooperated with the known germ line mutation. It is clear from knock out experiments in mice that MMR deficiency is compatible with normal growth and development, supporting these possibilities. Edelmann et al., Cell, 1996, 85, 1125 1134. Alternatively, it was possible that the mutant alleles exerted a dominant-negative effect, resulting in MMR deficiency even in the presence of the wild type allele of the corresponding MMR gene and all other genes involved in the MMR process. To distinguish between these possibilities, the truncated polypeptide encoded by the hPMS2 134 mutation was expressed in an MMR proficient cell line its affect on MMR activity was analyzed. The results showed that this mutant could indeed exert a dominant-negative effect, resulting in biochemical and genetic manifestations of MMR deficiency. One embodiment of the present invention is demonstrated in Table 1, where a Syrian hamster fibroblast cell line (TK) was transfected with an expression vector containing the hPMS2-134 (TK-PMS2-134) or the empty expression vector (TKvect), which also contains the NEO gene as a selectable marker. TK-PMS2-134 cells were determined to be stably expressing the gene via western blot analysis (data not shown). Nuclear lysates from hPMS2-134 and control cells were measured for the ability to correct mismatched DNA substrates. As shown in Table 1, TK-PMS2-134 cells had a dramatic decrease in repair activity while TKvect control cells were able to repair mismatched DNA duplexes at a rate of ~4.0 fmol/15 minutes (p<0.01).

TABLE 1

Relative endogenous MMR activity of MMR-proficient cells expressing an ectopically expressed morphogene or an empty expression vector

| Cell Lines | 5' DNA Repair activity of G/T mismatch (fmol/15 minutes) |
|---|---|
| TKvect | |
| 1 | 3.5 |
| 2 | 2.9 |
| 3 | 5.5 |
| TK-PMS2-134 | |
| 1 | 0 |
| 2 | 0 |
| 3 | 0.5 |

These data show that the expression of the TK-PMS2-134 results in suppressed MMR of a host organism and allows for an enhanced mutation rate of genetic loci with each mitosis.

Example 2 hPMS2-134 Can Alter Genes in vivo

An example of the ability to alter mismatch repair comes from experiments using manipulation of mismatch repair TK cells (described above) that expressed the TK-hPMS2-134 mutant were used by transfection of the mammalian expression construct containing a defective β-galactosidase gene (referred to as pCAR-OF) which was transfected into TK-hPMS2-134 or TKvect cells as described above. The pCAR OF vector consists of a β-galactosidase gene containing a 29-basepair poly-CA tract inserted at the 5' end of its coding region, which causes the wild-type reading frame to shift out-of-frame. This chimeric gene is cloned into the pCEP4, which contains the constitutively active cytomegalovirus (CMV) promoter upstream of the cloning site and also contains the hygromycin-resistance gene that allows for selection of cells containing this vector. The pCAR-OF reporter cannot generate β-galactosidase activity unless a frame-restoring mutation (i.e., insertion or deletion) arises following transfection into a host. Another reporter vector called pCAR-IF contains a β-galactosidase in which a 27-bp poly-CA repeat was cloned into the same site as the pCAR-OF gene, but it is biologically active because the removal of a single repeat restores the open reading frame and produces a functional chimeric β-galactosidase polypeptide (not shown). In these experiments, TK-hPMS2-134 and TKvect cells were transfected with the pCAR-OF reporter vector and selected for 17 days in neomycin plus hygromycin selection medium. After the 17 days, resistant colonies were stained for β-galactosidase production to determine the number of clones containing a genetically altered β-galactosidase gene. All conditions produced a relatively equal number of neomycin/hygromycin resistant cells, however, only the cells expressing the TK-hPMS2-134 contained a subset of clones that were positive for β-galactosidase activity. Representative results are shown in Table 2, which shows the data from these experiments where cell colonies were stained in situ for β-galactosidase activity and scored for activity. Cells were scored positive if the colonies turned blue in the presence of X-gal substrate and scored negative if colonies remained white. Analysis of triplicate experiments showed that a significant increase in the number of functional β-galactosidase positive cells was found in the TK-hPMS2-134 cultures, while no β-galactosidase positive cells were seen in the control TKvect cells.

TABLE 2

Number of TKmorph and TKvect cells containing functional β-galactosidase activity

| Cells | White Colonies | Blue Colonies | % Clones with altered B-gal |
|---|---|---|---|
| Tkvect | 65 +/− 9 | 0 | 0/65 = 0% |
| TK-PMS2-134 | 40 +/− 12 | 28 +/− 4 | 28/68 = 41% |

TK-PMS2-134/pCAR-OF clones that were pooled and expanded also showed a number of cells that contained a functional β-galactosidase gene. No β-galactosidase positive cells were observed in TKvect cells transfected with the pCAR-OF vector. These data are shown in FIG. 1 where the dark staining in panel B represent β-galactosidase positive cells present in the TK-PMS2-134/pCAR-OF cultures while none are found in the TKvect cells grown under similar conditions (panel A). These data demonstrate the ability of the mutant mismatch repair gene, hPMS2-134, to generate gene alterations in vivo, which allows for the rapid screening of clones with altered polypeptides exhibiting new biochemical features.

To confirm that alterations within the nucleotide sequences of the β-galactosidase gene was indeed responsible for the in vivo β-galactosidase activity present in TK-hPMS2-134 clones, RNA was isolated from TK-hPMS2-134/pCAR-OF and TKvect/pCAR-OF and the β-galactosidase mRNA primary structure was examined by reverse transcriptase polymerase chain reaction (RT-PCR) amplification and sequencing. Sequence analysis of β-galactosidase message from TKvect cells found no structural alterations in the input gene sequence. Analysis of the β-galactosidase message from TK-hPMS-134 cells found several changes within the coding sequences of the gene. These sequence alterations included insertion and deletions of the poly CA tract in the amino terminus as expected. Other alterations included insertions of sequences outside of the polyCA repeat as well as a series of single base alterations contained throughout the length of the gene.

Figure 2:
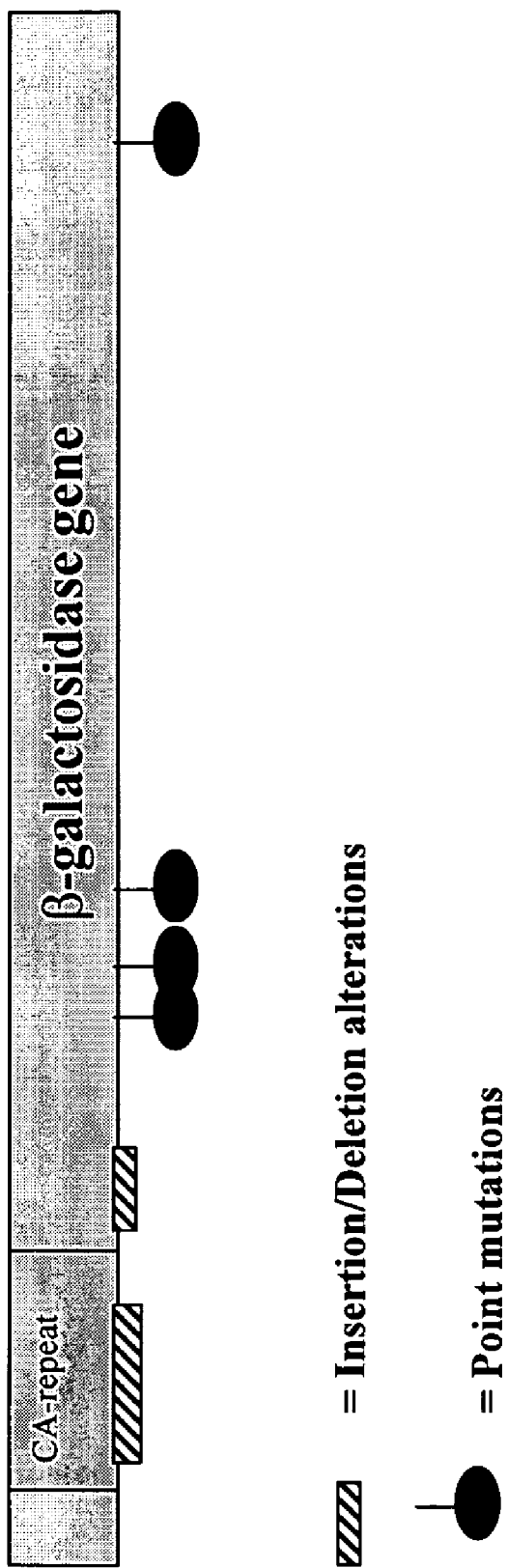
FIG. 2 is a schematic representation of sequence of alterations of the β-galactosidase gene produced by expression of TK-hPMS2-134 host cells in TK cells.

A summary of the genetic alterations are given in FIG. 2 where a schematic representation of the β-galactosidase gene is shown with the regions and types of genetic alterations depicted below.

Plasmids. The full length wild type hPMS2 cDNA was obtained from a human Hela cDNA library as described in Strand et al., Nature, 1993, 365, 274 276, which is incorporated herein by reference in its entirety. An hPMS2 cDNA containing a termination codon at amino acid 134 was obtained via RT PCR from the patient in which the mutation was discovered. Nicolaides et al., Mol. Cell. Biol., 1998, 18, 1635–1641, which is incorporated herein by reference in its entirety. The cDNA fragments were cloned into the BamHI site into the pSG5 vector, which contains an SV40 promoter followed by an SV40 polyadenylation signal. Nicolaides et al., Genomics, 1995, 29, 329 334, which is incorporated herein by reference in its entirety. The pCAR reporter vectors described in FIG. 1 were constructed as described in Palombo et al., Nature, 1994, 36, 417, which is incorporated herein by reference in its entirety.

β-galactosidase assay. Seventeen days following transfection with pCAR, β-galactosidase assays were performed using 20 μg of protein in 45 mM 2 mercaptoethanol, 1 mM $MgCl_2$, 0.1 M $NaPO_4$ and 0.6 mg/ml Chlorophenol red β-D galatopyranoside (CPRG, Boehringer Mannheim). Reactions were incubated for 1 hour, terminated by the addition of 0.5 M $Na_2CO_3$, and analyzed by spectrophotometry at 576 nm. Nicolaides et al., Mol. Cell. Biol., 1998, 18, 1635–1641. For in situ β-galactosidase staining, cells were fixed in 1% glutaraldehyde in PBS and incubated in 0.15 M NaCl, 1 mM $MgCl_2$, 3.3 mM $K_4Fe(CN)_6$, 3.3 mM $K_3Fe(CN)_6$, 0.2% X Gal for 2 hours at 37° C.

Example 3 hPMS2-134 Causes a Defect in MMR Activity

The differences in β-galactosidase activity between PMS2 WT and PMS2 134 transfected cells can be due to the PMS2 134 protein disturbing MMR activity resulting in a higher frequency of mutation within the pCAR OF reporter and re establishing the ORF. To directly test whether MMR was altered, a biochemical assay for MMR with the individual clones described in Example 1 was employed. Nuclear extracts were prepared from the clones and incubated with heteroduplex substrates containing either a /CA\ insertion deletion or a G/T mismatch under conditions described previously. The /CA\ and G/T heteroduplexes were used to test repair from the 3' and 5' directions, respectively. There was a dramatic difference between the PMS2-134 expressing clones and the other clones in these assays (Table 3).

TABLE 3

MMR activity of nuclear extracts from SH clones or pooled culturesa

| | Amt of repaired substrate (fmol/15 min) | |
|---|---|---|
| Cell line | 3'/CA\3'G/T 5' G/T 3'/CTG\ | 5'/CTG\ |
| SH clonesb | | |
| PMS2-NOT | | |
| Clone A | 10.2 | 3.5 |
| Clone B | 12.7 | 2.9 |
| Clone C | 13.5 | 5.5 |
| PMS2-WT | | |
| Clone A | 2.8 | 2.2 |
| Clone B | 5.7 | 4.8 |
| Clone c | 4.7 | 2.9 |
| PMS2-134 | | |
| Clone A | 2.5 | 0.0 |
| Clone B | 2.4 | 0.0 |
| Clone C | 5.0 | 0.5 |

| Pooled cultures | | | | |
|---|---|---|---|---|
| PMS2-NOT | 2.07 ± 0.09 | 2.37 ± 0.37 | 3.45 ± 1.35 | 2.77 ± 1.37 |
| PMS2-WT | 1.65 ± 0.94 | 1.86 ± 0.57 | 1.13 ± 0.23 | 1.23 ± 0.65 |
| PMS2-134 | 0.14 ± 0.2 | 0.0 ± 0.0 | 1.31 ± 0.66 | 0.0 ± 0.0 | aThe extracts were tested for MMR activity with 24 fmol of heteroduplex.
bThese data represent similar results derived from more than five independent experiments.

While all clones repaired substrates from the 3' direction (/CA\ heteroduplex), cells expressing the PMS2 134 polypeptide had very little 5' repair activity. A similar directional defect in mismatch repair was evident with pooled clones resulting from PMS2 134 transfection, or when the heteroduplex contained a 2 4 base pair loop, examples of which are shown in Table 3. A small decrease in MMR activity was observed in the 3' /CA\ PMS2-WT repair assays, perhaps a result of interference in the biochemical assays by over-expression of the PMS2 protein. No significant activity was caused by PMS2-WT in the in situ β-galactosidase assays, a result more likely to reflect the in vivo condition.

Biochemical assays for mismatch repair. MMR activity in nuclear extracts was performed as described, using 24 fmol of substrate, in Bronner et al., Nature, 1994, 368, 258 261 and Nicolaides et al., Mol. Cell. Biol., 1998, 18, 1635–1641, each of which is incorporated herein by reference in its entirety. Complementation assays were done by adding ~100 ng of purified MutL" or MutS" components to 100 μg of nuclear extract, adjusting the final KCl concentration to 100 mM. Bevins, Ciba Found. Symp., 1994, 186, 250–69 and Alderson et al., Res. Microbiol., 1993, 144, 665–72. The substrates used in these experiments contain a strand break 181 nucleotides 5' or 125 nucleotides 3' to the mismatch. Values represent experiments performed at least in duplicate.

Example 4

C-Terminus of hPMS2 Mediates Interaction Between hPMS2 and hMLH1

Figure 3:
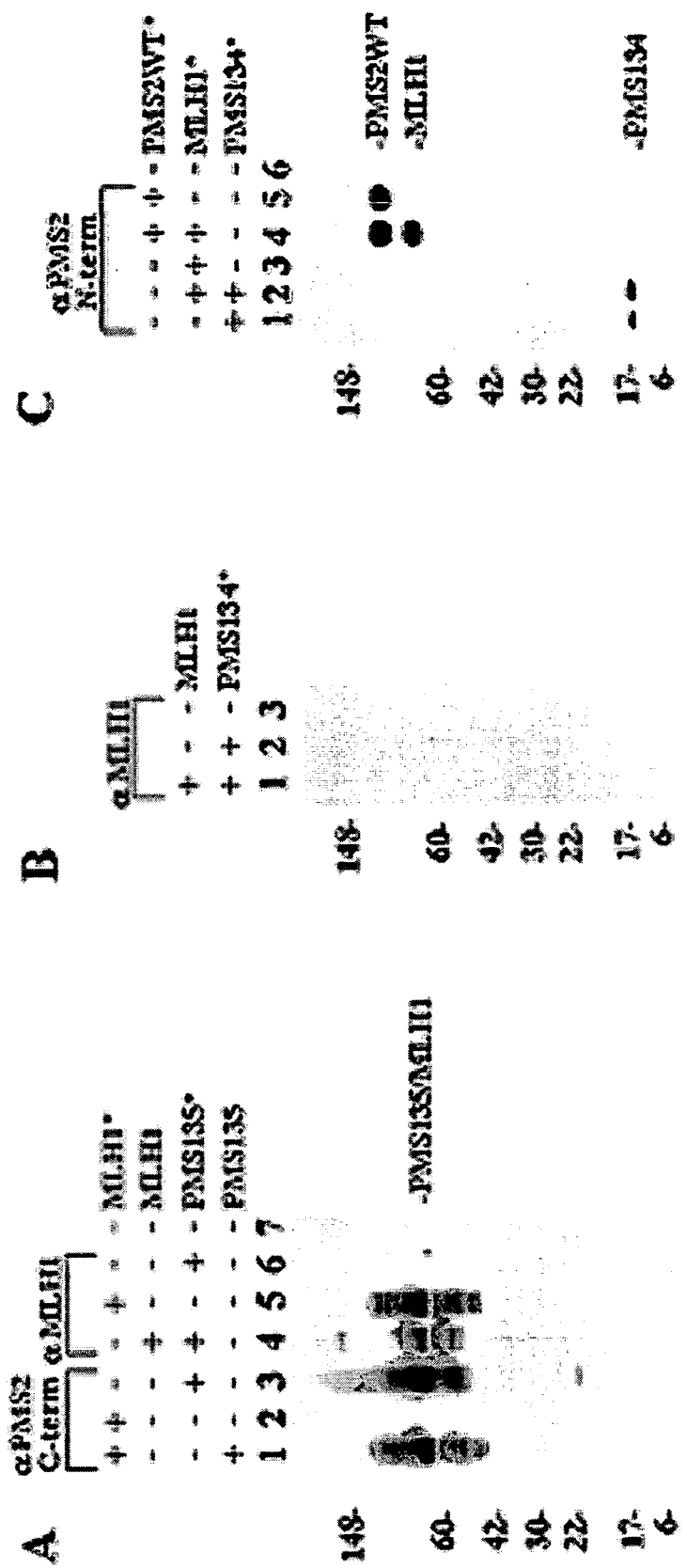
FIGS. 3A, 3B and 3C show a representative immunoprecipitation of in vitro translated hPMS2 and hMLH1 proteins.

To elucidate the mechanism by which hPMS2 134 affected MMR, the interaction between hPMS2 and hMLH1 was analyzed. Previous studies have shown that these two proteins dimerize to form a functionally active complex. Bronner et al., Nature, 1994, 368, 258 261. Proteins were synthesized in vitro using reticulocyte lysates, employing RNA generated from cloned templates. The full length hMLH1 and hPMS2 proteins bound to each other and were co precipitated with antibodies to either protein, as expected (data not shown). To determine the domain of hPMS2 that bound to hMLH1, the amino terminus (codons 1–134 ), containing the most highly conserved domain among mutL proteins (Su et al., J. Biol. Chem., 1988, 263, 6829 6835 and Edelmann et al., Cell, 1996, 85, 1125 1134 ), and the carboxyl terminus (codons 135–862) were separately cloned and proteins produced in vitro in coupled transcription translation reactions. FIGS. 3A, 3B, and 3C show a representative immunoprecipitation of in vitro-translated hPMS2 and hMLH1 proteins. FIG. 3A shows labeled (indicated by an asterisk) or unlabelled proteins incubated with an antibody to the C-terminus of hPMS2 in lanes 1 to 3 and to hMLH1 in lanes 4 to 6. Lane 7 contains a nonprogrammed reticulocyte lysate. PMS2-135 contains codons 135 to 862 of hPMS2. The major translation products of hPMS2 and hMLH1 are indicated. FIG. 3B shows labeled hPMS2-134 (containing codons 1–134 of hPMS2) incubated in the presence or absence of unlabelled hMLH1 plus an antibody to hMLH1 (lanes 1 and 2, respectively). Lane 3 contains lysate from a nonprogrammed reticulolysate. FIG. 3C shows labeled proteins incubated with an antibody to the N terminus of hPMS2. Lane 6 contains a nonprogrammed reticulocyte lysate. In both panels A and B, autoradiographs of immunoprecipitated products are shown. When a 35S labelled, full-length hMLH1 protein (FIG. 3A, lane 5) was mixed with the unlabelled carboxyl terminal hPMS2 polypeptide, a monoclonal antibody (mAb) to the carboxyl terminus of hPMS2 efficiently immunoprecipitated the labeled hMLH1 protein (lane 1). No hMLH1 protein was precipitated in the absence of hPMS2 (lane 2). Conversely, when the 35S labelled carboxyl terminus of hPMS2 (lane 3) was incubated with unlabelled, full length hMLH1 protein, an anti hMLH1 mAb precipitated the hPMS2 polypeptide (lane 4). In the absence of the unlabelled hMLH1 protein, no hPMS2 protein was precipitated by this mAb (lane 6). The same antibody failed to immunoprecipitate the amino terminus of hPMS2 (amino acids 1 134 ) when mixed with unlabelled MLH1 protein (FIG. 3B, lane 1). This finding was corroborated by the converse experiment in which radiolabelled hPMS2-134 (FIG. 3C, lane 1) was unable to coprecipitate radiolabelled MLH1 when precipitations were done using an N terminal hPMS2 antibody (FIG. 3C, lane 2) while this antibody was shown to be able to coprecipitate MLH1 when mixed with wild type hPMS2 (FIG. 3C, lane 4).

Figure 4:
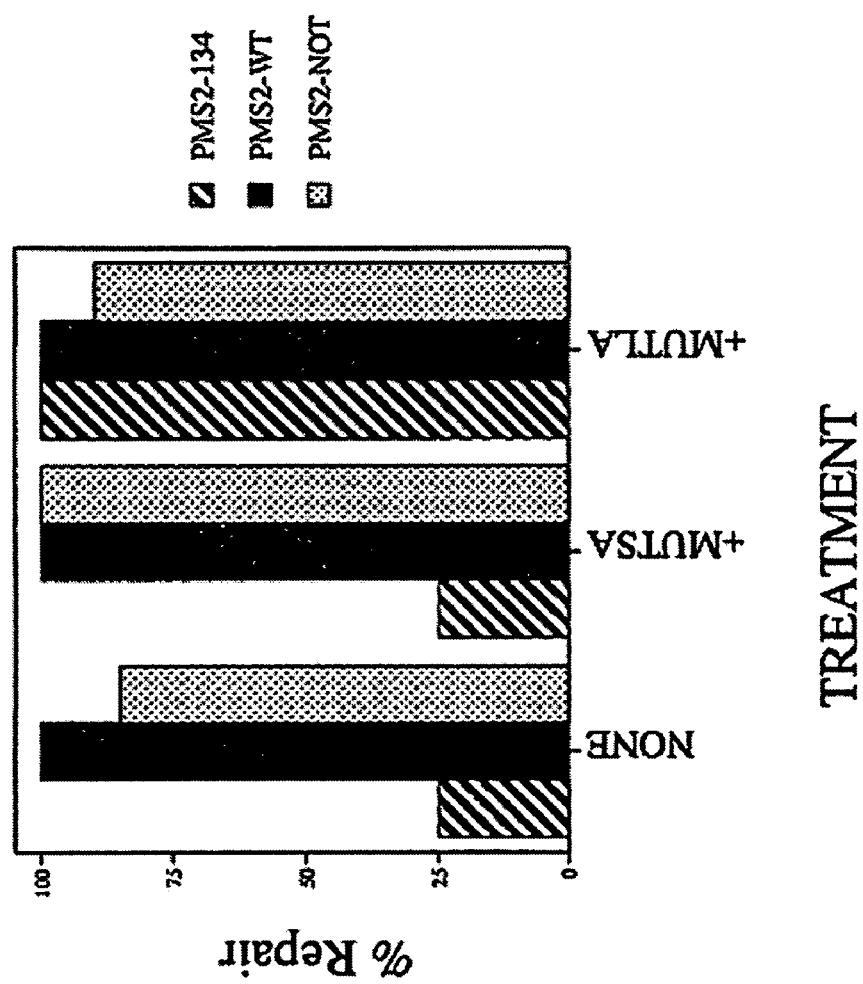
FIG. 4 shows representative complementation of MMR activity in transduced SH cells.

The initial steps of MMR are dependent on two protein complexes, called MutS" and MutL". Drummond et al., Science, 1995, 268, 1909 1912. As the amino terminus of hPMS2 did not mediate binding of hPMS2 to hMLH1, it was of interest to determine whether it might instead mediate the interaction between the MutL" complex (comprised of hMLH1 and hPMS2) and the MutS" complex (comprised of MSH2 and GTBP). Because previous studies have demonstrated that MSH2 and the MutL" components do not associate in solution, direct hPMS2-134:MutS" interaction was unable to be assayed. A different approach was used to address this issue, and attempted to complement nuclear extracts from the various SH cell lines with MutS" or MutL". If the truncated protein present in the PMS2-134 expressing SH cells was binding to MutS" and lowering its effective concentration in the extract, then adding intact MutS" should rescue the MMR defect in such extracts. FIG. 4 shows complementation of MMR activity in transduced SH cells. Lysates from pooled clones stably transduced with PMS2-NOT, PMS2-WT, or PMS2-134 were complemented with purified MutS" or MutL" MMR components by using the 5' G/T heteroduplex substrate. The values are presented as the percentage of repair activity in each case compared to that in lysates complemented with both purified MutL" and MutS" components to normalize for repair efficiency in the different lysate backgrounds. The values shown represent the average of at least three different determinations. Purified MutS" added to such extracts had no effect (FIG. 4). In contrast, addition of intact MutL" to the extract completely restored directional repair to the extracts from PMS2-134 cells (FIG. 4).

The results described above lead to several conclusions. First, expression of the amino terminus of hPMS2 results in an increase in microsatellite instability, consistent with a replication error (RER) phenotype. That this elevated microsatellite instability is due to MMR deficiency was proven by evaluation of extracts from stably transduced cells. Interestingly, the expression of PMS2-134 resulted in a polar defect in MMR, which was only observed using heteroduplexes designed to test repair from the 5' direction (no significant defect in repair from the 3' direction was observed in the same extracts). Interestingly, cells deficient in hMLH1 also have a polar defect in MMR, but in this case preferentially affecting repair from the 3' direction. Huttner et al., Pediatr. Res., 1999, 45, 785–94. It is known from previous studies in both prokaryotes and eukaryotes that the separate enzymatic components mediate repair from the two different directions. Our results indicate a model in which 5' repair is primarily dependent on hPMS2 while 3' repair is primarily dependent on hMLH1. It is easy to envision how the dimeric complex between PMS2 and MLH1 might set up this directionality. The combined results also demonstrate that a defect in directional MMR is sufficient to produce a RER+ phenotype.

The dominant-negative function of the PMS2-134 polypeptide can result from its binding to MLH1 and consequent inhibition of MutL" function. This is based in part on the fact that the most highly conserved domain of the PMS2 gene is located in its amino terminus, and the only known biochemical partner for PMS2 is MLH1. The binding studies revealed, however, that the carboxyl terminus of PMS2, rather than the highly conserved amino terminus, actually mediated binding to MLH1. This result is consistent with those recently obtained in S. cerevisciae, in which the MLH1 interacting domain of PMS1 (the yeast homolog of human PMS2) was localized to its carboxyl terminus. Leach et al., *Cell*, 1993, 75, 1215 1225. The add back experiments additionally showed that the hPMS2-134 mutant was not likely to mediate an interaction with the MutS" complex (FIG. 4). The hPMS2-134 polypeptide does not inhibit the initial steps in MMR, but rather interacts with and inhibits a downstream component of the pathway, perhaps a nuclease required for repair from the 5' direction.

The demonstration that the hPMS2-134 mutation can confer a dominant-negative MMR defect to transfected cells helps to explain the phenotype of the kindred in which this mutant was discovered. Three individuals from this kindred were found to carry the mutation, a father and his two children. Both children exhibited microsatellite instability in their normal tissues and both developed tumors at an early age, while the father had no evidence of microsatellite instability in his normal cells and was completely healthy at age 35. The only difference known to us with respect to the MMR genes in this family is that the father's mutant allele was expressed at lower levels than the wild type allele as assessed by sequencing of RT PCR products of RNA from lymphocytes. The children expressed both alleles at approximately equal levels. The dominant negative attribute of the hPMS2-134 mutant may only be manifest when it is present at sufficient concentrations (at least equimolar) thus, explaining the absence of MMR deficiency in the father. The reason for the differential expression of the hPMS2-134 allele in this kindred is not clear, though imprinting is a possibility. Ascertainment of additional, larger kindreds with such mutations will facilitate the investigation of this issue.

Western blots. Equal number of cells were lysed directly in lysis buffer (60 mM Tris, pH 6.8, 2% SDS, 10% glycerol, 0.1 M 2 mercaptoethanol, 0.001% bromophenol blue) and boiled for 5 minutes. Lysate proteins were separated by electrophoresis on 4 12% Tris glycine gels (for analysis of full length hPMS2) or 4 20% Tris glycine gels (for analysis of hPMS2-134). Gels were electroblotted onto Immobilon P (Millipore) in 48 mM Tris base, 40 mM glycine, 0.0375% SDS, 20% methanol and blocked overnight at 4° C. in Tris buffered saline plus 0.05% Tween 20 and 5% condensed milk. Filters were probed with a polyclonal antibody generated against residues 2–20 of hPMS2 (Santa Cruz Biotechnology, Inc.) and a horseradish peroxidase conjugated goat anti rabbit secondary antibody, using chemiluminescence for detection (Pierce).

In vitro translation. Linear DNA fragments containing hPMS2 and hMLH1 cDNA sequences were prepared by PCR, incorporating sequences for in vitro transcription and translation in the sense primer. A full length hMLH1 fragment was prepared using the sense primer 5' ggatcctaatacgactcactatagggagaccaccatgtcgttcgtggcaggg 3' (SEQ ID NO:1) (codons 1–6) and the antisense primer 5' taagtcttaagtgctaccaac 3' (SEQ ID NO:2) (located in the 3' untranslated region, nt 2411 2433), using a wild type hMLH1 cDNA clone as template. A full length hPMS2 fragment was prepared with the sense primer 5' ggatcctaatacgactcactataggagaccaccatggaacaattgcctgcgg 3' (SEQ ID NO:3) (codons 1–6) and the antisense primer 5' aggttagtgaagactctgtc 3' (SEQ ID NO:4) (located in 3' untranslated region, nt 2670 2690) using a cloned hPMS2 cDNA as template. A fragment encoding the amino terminal 134 amino acids of hPMS2 was prepared using the same sense primer and the antisense primer 5' agtcgagttccaaccttcg 3' (SEQ ID NO:5). A fragment containing codons 135–862 of hPMS135 was generated using the sense primer 5' ggatcctaatacgactcactataggagaccaccatgatgtttgatcacaatgg 3' (SEQ ID NO:6) (codons 135–141) and the same antisense primer as that used for the full length hPMS2 protein. These fragments were used to produce proteins via the coupled transcription translation system (Promega). The reactions were supplemented with $^{35}S$ labelled methionine or unlabelled methionine, as indicated in the text. The PMS135 and hMLH1 proteins could not be simultaneously radiolabelled and immunoprecipitated because of their similar molecular weights precluded resolution. Lower molecular weight bands are presumed to be degradation products and/or polypeptides translated from alternative internal methionines.

Immunoprecipitation. Immunoprecipitations were performed on in vitro translated proteins by mixing the translation reactions with 1 μg of the MLH1 specific monoclonal antibody (mAB) MLH14 (Oncogene Science, Inc.), a polyclonal antibody generated to codons 2–20 of hPMS2 described above, or a polyclonal antibody generated to codons 843–862 of hPMS2 (Santa Cruz Biotechnology, Inc.) in 400:1 of EBC buffer (50 mM Tris, pH 7.5, 0.1 M NaCl, 0.5% NP40). After incubation for 1 hour at 4° C., protein A sepharose (Sigma) was added to a final concentration of 10% and reactions were incubated at 4° C. for 1 hour. Proteins bound to protein A were washed five times in EBC and separated by electrophoresis on 4 20% Tris glycine gels, which were then dried and autoradiographed.

Example 5

Syrian Hamster Tk-ts-13 Cells Produce a Novel Anti-Microbial Polypeptide Can Suppress the Growth of *Bacillus subtilis*

Figure 5:
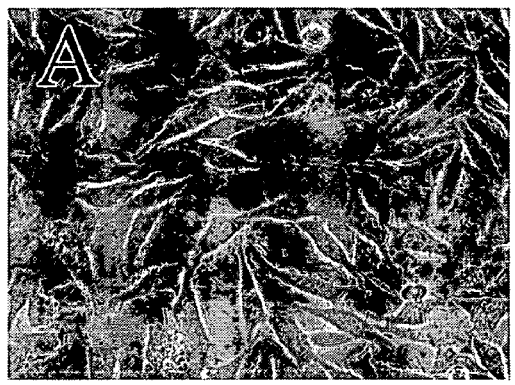
FIG. 5 is a representative photograph of Syrian hamster TK-ts13 cells transfected with a eukaryotic expression vector that produces a novel anti-microbial polypeptide.
Figure 5:
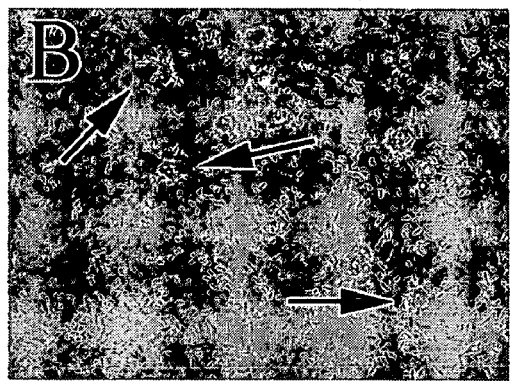

The feasibility of creating microbial-resistant mammalian cells is demonstrated as follows. Syrian Hamster TK fibroblasts were transfected with a mammalian expression vector containing a novel anti-microbial polypeptide called mlg1 or the empty expression vector called psg. When cells expressing the mlg polypeptide (referred to as TK-mlg1) were grown in the presence of *Bacillus subtilis*, these cells were able to suppress the growth of the microbes and allow the TK host to remain viable in contrast to TK cells transfected with the empty vector (TK=psg), which all died from the toxic effects that *Bacillus subtilis* has on mammalian cells. FIG. 5 shows a photograph of TK-mlg1 and TK=psg cultures grown in the presence of *Bacillus* for 4 days. Syrian hamster Tk-ts13 cells were transfected with a eukaryotic expression vector that produces a novel antimicrobial polypeptide referred to as mlg1 (Panel A) or the expression vector lacking an inserted cDNA for expression (TK=psg, Panel B). Cells were plated at a density of $5 \times 10^5$ cells/ml in a 10 cm falcon pyrogenic-free petri dish in growth medium for 24 hours and then inoculated with 10:1 of an exponentially growing culture of *Bacillus subtilis*. Cultures were then incubated for 4 days at which time Bacilli grow and begin to lyse the Tk-ts13 parental culture as shown in panel B (indicated by arrows), while cells expressing the antimicrobial mlg1polypeptide (Panel A) remain viable in the presence of *Bacillus* (small granular structures present in panels A and B). These data demonstrate the feasibility of cells to survive in the presence of *Bacillus* contamination when they produce an anti-microbial agent. These data show that antimicrobial producing mammalian cells are capable of growing and surviving in the presence of toxic microbes.

Cell lines and transfection. Syrian Hamster fibroblast Tk ts13 cells were obtained from ATCC and cultured as described. Modrich, Science, 1994, 266, 1959 1960. Stably transfected cell lines expressing hPMS2 were created by cotransfection of the PMS2 expression vectors and the pLHL4 plasmid encoding the hygromycin resistance gene at a ratio of 3:1 (pCAR:pLHL4) and selected with hygromycin. Stably transfected cell lines containing pCAR reporters were generated by co transfection of pCAR vectors together with either pNTK plasmid encoding the neomycin resistance plasmid or with pLHL4. All transfections were performed using calcium phosphate as previously described in Modrich, *Science*, 1994, 266, 1959 1960, which is incorporated herein by reference in its entirety.

Example 6

TK-hPMS2-134 Cells can Suppress the Growth of *Escherichia coli* in vitro

While TK-hPMS2-134 TK-ts13 cells have been previously shown to be capable of altering genes in vivo (refer to Table 2 and FIG. 1), the ability to generate "naturally microbial-resistant" clones has not been reported in the literature. To generate microbial-resistant TK cells, TK-ts13 cells constitutively expressing the a dominant-negative mismatch repair gene, TK-hPMS2-134 or the empty vector (TKvect) that have been in culture for >3 months (~60 passages) were seeded at $5 \times 10^5$ cells/ml in Dulbeicco's Modified Eagles Medium (DMEM) plus 10% fetal bovine serum (FBS) and plated into 10 cm dishes (Falcon) in duplicate. These cells were grown overnight at 37° C. in 5% CO2 to allow cells to adhere to the plastic. The next day, TK cultures were inoculated with 10:1 of an exponentially growing culture of *Escherichia coli*. Cultures were then grown at 37° C. in 5% CO2 and observed on day 7 and 14 for microbial-resistant cell clones; these cells appear as clones of cells surrounded by "cleared" areas on the plate. At day 7, all cells in the control transfected TKvect culture were dead, while a subset of cells were viable in the TK-hPMS2-134 transfected cultures. At day 14, there were no clones in the control transfected TKvect cultures, while there were 34 and 40 *Escherichia coli*-resistant colonies formed in the TK-hPMS2-134 transfected cultures. Growing clones from each dish were then pooled as individual cultures and grown to confluence. These cultures were named TK-hPMS2-134 (R1) and TK-hPMS2-134 (R2). Cultures were cured of *Escherichia coli* by the addition of 1 mg/ml G418, in which the TK-hPMS2-134 cells are resistant due to expression of the neomycin-resistance gene contained on the mammalian expression vector used to generate the cells.

Figure 6:
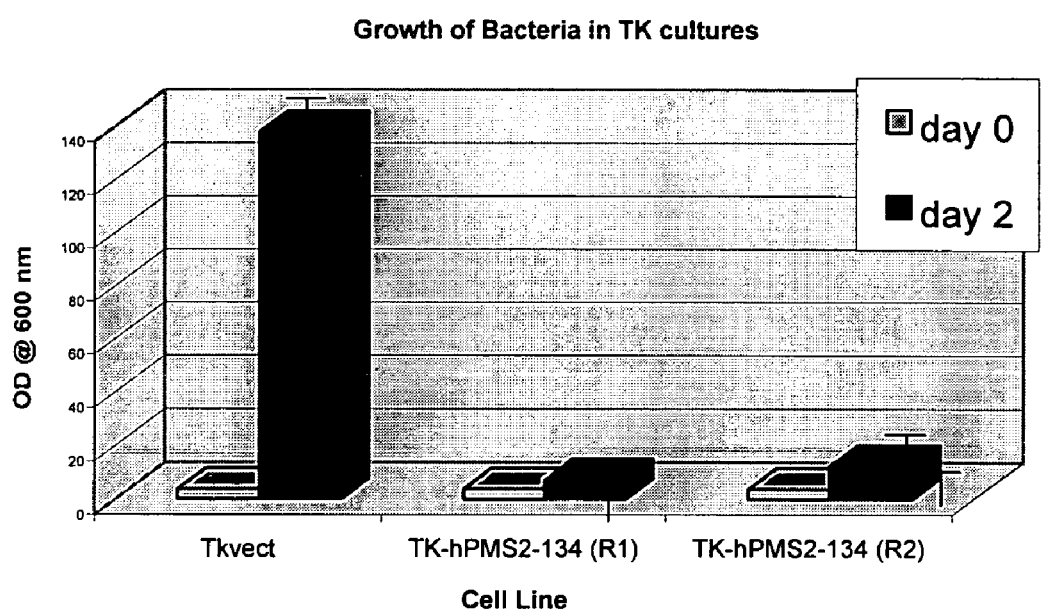
FIG. 6 is a representative graph showing TK-hPMS-134 transfected TK cells can suppress the growth of bacteria in vitro.

TKvect, TK-hPMS2-134 (1) and TK-hPMS2-134 (R2) cells were plated at $5 \times 10^5$ cell/ml in 10 mls and plated into 10 cm dishes in duplicate. The next day, 10:1 of a logarithmic stage *Escherichia coli* culture was added to each TK culture and cultures were grown for 48 hours at 37° C. in 5% $CO_2$. An aliquot of supernatant from each culture was harvested immediately after inoculation to establish a baseline density of bacteria for each culture. After 48 hours, 2 ml of supernatant were harvested from each culture as well as from uninfected TK cultures. One ml of each supernatant was then analyzed by a spectrophotometer at an $OD_{600}$ to measure for bacterial density. Supernatants from uninfected cultures were used as a blank to correct for background. As shown in FIG. 6, bacterial growth was significantly suppressed in TK-hPMS2-134 (R1) and TK-hPMS2-134 (R2) cultures in contrast to TKvect control cells. These data demonstrate the feasibility of using a dominant-negative mismatch repair mutant hPMS2-134 on mammalian cells to produce genetically altered clones capable of producing a molecule(s) that can suppress microbial growth.

As those skilled in the art will appreciate, numerous changes and modifications may be made to the preferred embodiments of the invention without departing from the spirit of the invention. It is intended that all such variations fall within the scope of the invention. In addition, the entire disclosure of each publication cited herein is hereby incorporated herein by reference.

What is claimed is:

1. A method for obtaining a genetically stable mammalian cell that is resistant to a selected microbe comprising:

growing a culture of mammalian cells wherein said cells comprise a dominant-negative allele of a mismatch repair gene, wherein said mismatch repair gene encodes the first 133 amino acids of PMS2, and allowing mutations to occur;

exposing said cells to said selected microbe;

selecting said mammalian cell that is resistant to said selected microbe; and suppressing expression of said dominant negative allele of said mismatch repair gene; thereby obtaining a genetically stable mammalian cell that is resistant to a selected microbe.

2. The method of claim 1 wherein said mammalian cell is selected for resistance to a bacterium.

3. The method of claim 1 wherein said mammalian cell is selected for resistance to a fungus.

4. The method of claim 1 wherein said dominant negative allele of said mismatch repair gene is operably linked to an inducible promoter.

5. The method of claim 4 wherein expression of said dominant negative allele is suppressed by withdrawing an inducer of said inducible promoter.

6. The method of claim 1 wherein expression of said dominant negative allele is suppressed by knocking out said dominant negative allele.

7. The method of claim 1 wherein said step of selecting for microbial resistance comprises isolating and testing culture medium from said hypermutable cell.

* * * * *

SEQUENCE LISTING

<160> NUMBER OF SEQ ID NOS: 18

<210> SEQ ID NO 1
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 1
ggatcctaat acgactcact atagggagac caccatgtcg ttcgtggcag gg            52

<210> SEQ ID NO 2
<211> LENGTH: 21
<212> TYPE: DNA
<213> ORGANISM: Artificial Sequence
<220> FEATURE:

<223> OTHER INFORMATION: Oligonucleotide primer

<400> SEQUENCE: 2
taagtcttaa gtgctaccaa c                                      21

<210> SEQ ID NO 3
<211> LENGTH: 53
<212> TYPE: DNA
<213> ORGANISM: Artificial Sequence
<220> FEATURE:
<223> OTHER INFORMATION: Oligonucleotide primer

<400> SEQUENCE: 3
ggatcctaat acgactcact atagggagac caccatggaa caattgcctg cgg    53

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 4
aggttagtga agactctgtc                                        20

<210> SEQ ID NO 5
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 5
agtcgagttc caaccttcg                                         19

<210> SEQ ID NO 6
<211> LENGTH: 54
<212> TYPE: DNA
<213> ORGANISM: Artificial Sequence
<220> FEATURE:
<223> OTHER INFORMATION: Oligonucleotide primer

<400> SEQUENCE: 6
ggatcctaat acgactcact atagggagac caccatgatg tttgatcaca atgg   54

<210> SEQ ID NO 7
<211> LENGTH: 859
<212> TYPE: PRT
<213> ORGANISM: Mus musculus

<400> SEQUENCE: 7

Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
            20                  25                  30

Leu Ser Leu Ser Thr Ala Val Lys Glu Leu Ile Glu Asn Ser Val Asp
        35                  40                  45

Ala Gly Ala Thr Thr Ile Asp Leu Arg Leu Lys Asp Tyr Gly Val Asp
    50                  55                  60

Leu Ile Glu Val Ser Asp Asn Gly Cys Gly Val Glu Glu Asn Phe
65                  70                  75                  80

Glu Gly Leu Ala Leu Lys His His Thr Ser Lys Ile Gln Glu Phe Ala
                85                  90                  95

-continued

```
Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125

Ala Ser Val Gly Thr Arg Leu Val Phe Asp His Asn Gly Lys Ile Thr
    130                 135                 140

Gln Lys Thr Pro Tyr Pro Arg Pro Lys Gly Thr Thr Val Ser Val Gln
145                 150                 155                 160

His Leu Phe Tyr Thr Leu Pro Val Arg Tyr Lys Glu Phe Gln Arg Asn
                165                 170                 175

Ile Lys Lys Glu Tyr Ser Lys Met Val Gln Val Leu Gln Ala Tyr Cys
            180                 185                 190

Ile Ile Ser Ala Gly Val Arg Val Ser Cys Thr Asn Gln Leu Gly Gln
        195                 200                 205

Gly Lys Arg His Ala Val Cys Thr Ser Gly Thr Ser Gly Met Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ala Val Cys Glu Glu Tyr Gly
                245                 250                 255

Leu Ser Thr Ser Gly Arg His Lys Thr Phe Ser Thr Phe Arg Ala Ser
            260                 265                 270

Phe His Ser Ala Arg Thr Ala Pro Gly Gly Val Gln Gln Thr Gly Ser
        275                 280                 285

Phe Ser Ser Ile Arg Gly Pro Val Thr Gln Gln Arg Ser Leu Ser
290                 295                 300

Leu Ser Met Arg Phe Tyr His Met Tyr Asn Arg His Gln Tyr Pro Phe
305                 310                 315                 320

Val Val Leu Asn Val Ser Val Asp Ser Glu Cys Val Asp Ile Asn Val
                325                 330                 335

Thr Pro Asp Lys Arg Gln Ile Leu Leu Gln Glu Lys Leu Leu Leu
            340                 345                 350

Ala Val Leu Lys Thr Ser Leu Ile Gly Met Phe Asp Ser Asp Ala Asn
        355                 360                 365

Lys Leu Asn Val Asn Gln Gln Pro Leu Leu Asp Val Glu Gly Asn Leu
    370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
            420                 425                 430

Ile Lys Ser Arg Gly Pro Glu Thr Ala Glu Leu Thr Arg Ser Phe Pro
        435                 440                 445

Ser Glu Lys Arg Gly Val Leu Ser Ser Tyr Pro Ser Asp Val Ile Ser
    450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
                485                 490                 495

Leu Ser Ser Thr Ser Ala Gly Ser Glu Glu Phe Ser Thr Pro Glu
            500                 505                 510
```

```
Val Ala Ser Ser Phe Ser Ser Asp Tyr Asn Val Ser Ser Leu Glu Asp
            515                 520                 525

Arg Pro Ser Gln Glu Thr Ile Asn Cys Gly Asp Leu Asp Cys Arg Pro
        530                 535                 540

Pro Gly Thr Gly Gln Ser Leu Lys Pro Glu Asp His Gly Tyr Gln Cys
545                 550                 555                 560

Lys Ala Leu Pro Leu Ala Arg Leu Ser Pro Thr Asn Ala Lys Arg Phe
                565                 570                 575

Lys Thr Glu Glu Arg Pro Ser Asn Val Asn Ile Ser Gln Arg Leu Pro
            580                 585                 590

Gly Pro Gln Ser Thr Ser Ala Ala Glu Val Asp Val Ala Ile Lys Met
        595                 600                 605

Asn Lys Arg Ile Val Leu Leu Glu Phe Ser Leu Ser Ser Leu Ala Lys
            610                 615                 620

Arg Met Lys Gln Leu Gln His Leu Lys Ala Gln Asn Lys His Glu Leu
625                 630                 635                 640

Ser Tyr Arg Lys Phe Arg Ala Lys Ile Cys Pro Gly Glu Asn Gln Ala
                645                 650                 655

Ala Glu Asp Glu Leu Arg Lys Glu Ile Ser Lys Ser Met Phe Ala Glu
            660                 665                 670

Met Glu Ile Leu Gly Gln Phe Asn Leu Gly Phe Ile Val Thr Lys Leu
        675                 680                 685

Lys Glu Asp Leu Phe Leu Val Asp Gln His Ala Ala Asp Glu Lys Tyr
690                 695                 700

Asn Phe Glu Met Leu Gln Gln His Thr Val Leu Gln Ala Gln Arg Leu
705                 710                 715                 720

Ile Thr Pro Gln Thr Leu Asn Leu Thr Ala Val Asn Glu Ala Val Leu
                725                 730                 735

Ile Glu Asn Leu Glu Ile Phe Arg Lys Asn Gly Phe Asp Phe Val Ile
            740                 745                 750

Asp Glu Asp Ala Pro Val Thr Glu Arg Ala Lys Leu Ile Ser Leu Pro
        755                 760                 765

Thr Ser Lys Asn Trp Thr Phe Gly Pro Gln Asp Ile Asp Glu Leu Ile
770                 775                 780

Phe Met Leu Ser Asp Ser Pro Gly Val Met Cys Arg Pro Ser Arg Val
785                 790                 795                 800

Arg Gln Met Phe Ala Ser Arg Ala Cys Arg Lys Ser Val Met Ile Gly
                805                 810                 815

Thr Ala Leu Asn Ala Ser Glu Met Lys Lys Leu Ile Thr His Met Gly
            820                 825                 830

Glu Met Asp His Pro Trp Asn Cys Pro His Gly Arg Pro Thr Met Arg
        835                 840                 845

His Val Ala Asn Leu Asp Val Ile Ser Gln Asn
850                 855

<210> SEQ ID NO 8
<211> LENGTH: 3056
<212> TYPE: DNA
<213> ORGANISM: Mus musculus

<400> SEQUENCE: 8
gaattccggt gaaggtcctg aagaatttcc agattcctga gtatcattgg aggagacaga      60
taacctgtcg tcaggtaacg atggtgtata tgcaacagaa atgggtgttc ctggagacgc     120
gtcttttccc gagagcggca ccgcaactct cccgcggtga ctgtgactgg aggagtcctg     180
```

```
catccatgga gcaaaccgaa ggcgtgagta cagaatgtgc taaggccatc aagcctattg    240
atgggaagtc agtccatcaa atttgttctg ggcaggtgat actcagttta agcaccgctg    300
tgaaggagtt gatagaaaat agtgtagatg ctggtgctac tactattgat ctaaggctta    360
aagactatgg ggtggaccct cattgaagttt cagacaatgg atgtgggta aagaagaaa    420 actttgaagg tctagctctg aaacatcaca catctaagat tcaagagttt gccgacctca    480
cgcaggttga aactttcggc tttcgggggg aagctctgag ctctctgtgt gcactaagtg    540
atgtcactat atctacctgc cacggtctg caagcgttgg gactcgactg gtgtttgacc    600
ataatgggaa aatcacccag aaaactccct accccgacc taaaggaacc acagtcagtg    660
tgcagcactt atttataca ctacccgtgc gttacaaaga gtttcagagg aacattaaaa    720
aggagtattc caaaatggtg caggtcttac aggcgtactg tatcatctca gcaggcgtcc    780
gtgtaagctg cactaatcag ctcggacagg ggaagcggca cgctgtggtg tgcacaagcg    840
gcacgtctgg catgaaggaa aatatcgggt ctgtgtttgg ccagaagcag ttgcaaagcc    900
tcattccttt tgttcagctg cccctagta acgctgtgtg tgaagagtac ggcctgagca    960
cttcaggacg ccacaaaacc ttttctacgt ttcgggcttc atttcacagt gcacgcacgg   1020 cgccggagg agtgcaacag acaggcagtt tttcttcatc aatcagaggc cctgtgaccc   1080
agcaaaggtc tctaagcttg tcaatgaggt tttatcacat gtataaccgg catcagtacc   1140
catttgtcgt ccttaacgtt tccgttgact cagaatgtgt ggatattaat gtaactccag   1200
ataaaaggca aattctacta caagaagaga agctattgct ggccgttta aagacctcct   1260 tgataggaat gtttgacagt gatgcaaaca agcttaatgt caaccagcag ccactgctag   1320
atgttgaagg taacttagta aagctgcata ctgcagaact agaaaagcct gtgccaggaa   1380
agcaagataa ctctccttca ctgaagagca cagcagacga gaaagggta gcatccatct   1440 ccaggctgag agaggccttt tctcttcatc ctactaaaga gatcaagtct agggtccag   1500 agactgctga actgacacgg agttttccaa gtgagaaaag gggcgtgtta tcctcttatc   1560
cttcagacgt catctcttac agaggcctcc gtggctcgca ggacaaattg gtgagtccca   1620
cggacagccc tggtgactgt atggacagag agaaaataga aaagactca gggctcagca   1680 gcacctcagc tggctctgag gaagagttca gcacccaga agtggccagt agctttagca   1740
gtgactataa cgtgagctcc ctagaagaca gaccttctca ggaaaccata aactgtggtg   1800
acctggactg ccgtcctcca ggtacaggac agtccttgaa gccagaagac catggatatc   1860
aatgcaaagc tctacctcta gctcgtctgt cacccacaaa tgccaagcgc ttcaagacag   1920
aggaaagacc ctcaaatgtc aacatttctc aaagattgcc tggtcctcag agcacctcag   1980
cagctgaggt cgatgtagcc ataaaaatga ataagagaat cgtgctcctc gagttctctc   2040
tgagttctct agctaagcga atgaagcagt tacagcacct aaaggcgcag aacaaacatg   2100
aactgagtta cagaaaattt agggccaaga tttgccctgg agaaaaccaa gcagcagaag   2160
atgaactcag aaaagagatt agtaaatcga tgtttgcaga gatggagatc ttgggtcagt   2220
ttaacctggg atttatagta accaaactga agaggacct cttcctggtg gaccagcatg   2280
ctgcggatga gaagtacaac tttgagatgc tgcagcagca cacggtgctc caggcgcaga   2340
ggctcatcac accccagact ctgaacttaa ctgctgtcaa tgaagctgta ctgatagaaa   2400
atctggaaat attcagaaag aatgctttg actttgtcat tgatgaggat gctccagtca   2460
ctgaaagggc taaattgatt tccttaccaa ctagtaaaaa ctggacctttt ggaccccaag   2520
```

-continued

```
atatagatga actgatctttt atgttaagtg acagccctgg ggtcatgtgc cggccctcac    2580
gagtcagaca gatgtttgct tccagagcct gtcggaagtc agtgatgatt ggaacggcgc    2640
tcaatgcgag cgagatgaag aagctcatca cccacatggg tgagatggac caccCctgga    2700
actgccccca cggcaggcca accatgaggc acgttgccaa tctggatgtc atctctcaga    2760
actgacacac cccttgtagc atagagttta ttacagattg ttcggtttgc aaagagaagg    2820
ttttaagtaa tctgattatc gttgtacaaa aattagcatg ctgctttaat gtactggatc    2880
catttaaaag cagtgttaag gcaggcatga tggagtgttc ctctagctca gctacttggg    2940
tgatccggtg ggagctcatg tgagcccagg actttgagac cactccgagc acattcatg    3000 agactcaatt caaggacaaa aaaaaaaaga tattttttgaa gcctttttaaa aaaaaa      3056
```

<210> SEQ ID NO 9
<211> LENGTH: 862
<212> TYPE: PRT
<213> ORGANISM: Homo sapiens

<400> SEQUENCE: 9

```
Met Glu Arg Ala Glu Ser Ser Ser Thr Glu Pro Ala Lys Ala Ile Lys
 1               5                  10                  15

Pro Ile Asp Arg Lys Ser Val His Gln Ile Cys Ser Gly Gln Val Val
                20                  25                  30

Leu Ser Leu Ser Thr Ala Val Lys Glu Leu Val Glu Asn Ser Leu Asp
            35                  40                  45

Ala Gly Ala Thr Asn Ile Asp Leu Lys Leu Lys Asp Tyr Gly Val Asp
        50                  55                  60

Leu Ile Glu Val Ser Asp Asn Gly Cys Gly Val Glu Glu Glu Asn Phe
 65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
                100                 105                 110

Ser Leu Cys Ala Leu Ser Asp Val Thr Ile Ser Thr Cys His Ala Ser
            115                 120                 125

Ala Lys Val Gly Thr Arg Leu Met Phe Asp His Asn Gly Lys Ile Ile
        130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205

Gly Lys Arg Gln Pro Val Val Cys Thr Gly Gly Ser Pro Ser Ile Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
            260                 265                 270

Ile Ser Gln Cys Thr His Gly Val Gly Arg Ser Ser Thr Asp Arg Gln
        275                 280                 285
```

-continued

```
Phe Phe Phe Ile Asn Arg Arg Pro Cys Asp Pro Ala Lys Val Cys Arg
290                 295                 300
Leu Val Asn Glu Val Tyr His Met Tyr Asn Arg His Gln Tyr Pro Phe
305                 310                 315                 320
Val Val Leu Asn Ile Ser Val Asp Ser Glu Cys Val Asp Ile Asn Val
                325                 330                 335
Thr Pro Asp Lys Arg Gln Ile Leu Leu Gln Glu Glu Lys Leu Leu Leu
            340                 345                 350
Ala Val Leu Lys Thr Ser Leu Ile Gly Met Phe Asp Ser Asp Val Asn
        355                 360                 365
Lys Leu Asn Val Ser Gln Gln Pro Leu Leu Asp Val Glu Gly Asn Leu
370                 375                 380
Ile Lys Met His Ala Ala Asp Leu Glu Lys Pro Met Val Glu Lys Gln
385                 390                 395                 400
Asp Gln Ser Pro Ser Leu Arg Thr Gly Glu Glu Lys Lys Asp Val Ser
                405                 410                 415
Ile Ser Arg Leu Arg Glu Ala Phe Ser Leu Arg His Thr Thr Glu Asn
            420                 425                 430
Lys Pro His Ser Pro Lys Thr Pro Glu Pro Arg Arg Ser Pro Leu Gly
        435                 440                 445
Gln Lys Arg Gly Met Leu Ser Ser Ser Thr Ser Gly Ala Ile Ser Asp
450                 455                 460
Lys Gly Val Leu Arg Pro Gln Lys Glu Ala Val Ser Ser Ser His Gly
465                 470                 475                 480
Pro Ser Asp Pro Thr Asp Arg Ala Glu Val Glu Lys Asp Ser Gly His
                485                 490                 495
Gly Ser Thr Ser Val Asp Ser Glu Gly Phe Ser Ile Pro Asp Thr Gly
            500                 505                 510
Ser His Cys Ser Ser Glu Tyr Ala Ala Ser Ser Pro Gly Asp Arg Gly
        515                 520                 525
Ser Gln Glu His Val Asp Ser Gln Glu Lys Ala Pro Glu Thr Asp Asp
530                 535                 540
Ser Phe Ser Asp Val Asp Cys His Ser Asn Gln Glu Asp Thr Gly Cys
545                 550                 555                 560
Lys Phe Arg Val Leu Pro Gln Pro Thr Asn Leu Ala Thr Pro Asn Thr
                565                 570                 575
Lys Arg Phe Lys Lys Glu Glu Ile Leu Ser Ser Ser Asp Ile Cys Gln
            580                 585                 590
Lys Leu Val Asn Thr Gln Asp Met Ser Ala Ser Gln Val Asp Val Ala
        595                 600                 605
Val Lys Ile Asn Lys Lys Val Val Pro Leu Asp Phe Ser Met Ser Ser
610                 615                 620
Leu Ala Lys Arg Ile Lys Gln Leu His His Glu Ala Gln Gln Ser Glu
625                 630                 635                 640
Gly Glu Gln Asn Tyr Arg Lys Phe Arg Ala Lys Ile Cys Pro Gly Glu
                645                 650                 655
Asn Gln Ala Ala Glu Asp Glu Leu Arg Lys Glu Ile Ser Lys Thr Met
            660                 665                 670
Phe Ala Glu Met Glu Ile Ile Gly Gln Phe Asn Leu Gly Phe Ile Ile
        675                 680                 685
Thr Lys Leu Asn Glu Asp Ile Phe Ile Val Asp Gln His Ala Thr Asp
690                 695                 700
```

```
Glu Lys Tyr Asn Phe Glu Met Leu Gln Gln His Thr Val Leu Gln Gly
705                 710                 715                 720

Gln Arg Leu Ile Ala Pro Gln Thr Leu Asn Leu Thr Ala Val Asn Glu
            725                 730                 735

Ala Val Leu Ile Glu Asn Leu Glu Ile Phe Arg Lys Asn Gly Phe Asp
        740                 745                 750

Phe Val Ile Asp Glu Asn Ala Pro Val Thr Glu Arg Ala Lys Leu Ile
    755                 760                 765

Ser Leu Pro Thr Ser Lys Asn Trp Thr Phe Gly Pro Gln Asp Val Asp
770                 775                 780

Glu Leu Ile Phe Met Leu Ser Asp Ser Pro Gly Val Met Cys Arg Pro
785                 790                 795                 800

Ser Arg Val Lys Gln Met Phe Ala Ser Arg Ala Cys Arg Lys Ser Val
            805                 810                 815

Met Ile Gly Thr Ala Leu Asn Thr Ser Glu Met Lys Lys Leu Ile Thr
        820                 825                 830

His Met Gly Glu Met Asp His Pro Trp Asn Cys Pro His Gly Arg Pro
    835                 840                 845

Thr Met Arg His Ile Ala Asn Leu Gly Val Ile Ser Gln Asn
850                 855                 860

<210> SEQ ID NO 10
<211> LENGTH: 2771
<212> TYPE: DNA
<213> ORGANISM: Homo sapiens

<400> SEQUENCE: 10
cgaggcggat cgggtgttgc atccatggag cgagctgaga gctcgagtac agaacctgct      60
aaggccatca aacctattga tcggaagtca gtccatcaga tttgctctgg gcaggtggta     120
ctgagtctaa gcactgcggt aaaggagtta gtagaaaaca gtctggatgc tggtgccact     180
aatattgatc taaagcttaa ggactatgga gtggatctta ttgaagtttc agacaatgga     240
tgtggggtag aagaagaaaa cttcgaaggc ttaactctga acatcacaca atctaagatt     300
caagagtttg ccgacctaac tcaggttgaa acttttggct tcgggggga agctctgagc     360 tcactttgtg cactgagcga tgtcaccatt tctacctgcc acgcatcggc gaaggttgga     420
actcgactga tgtttgatca caatgggaaa attatccaga aaacccccta cccccgcccc     480
agagggacca cagtcagcgt gcagcagtta ttttccacac tacctgtgcg ccataaggaa     540
tttcaaagga atattaagaa ggagtatgcc aaaatggtcc aggtcttaca tgcatactgt     600
atcatttcag caggcatccg tgtaagttgc accaatcagc ttggacaagg aaaacgacag     660
cctgtggtat gcacaggtgg aagccccagc ataaggaaa atatcggctc tgtgtttggg     720
cagaagcagt tgcaaagcct cattcctttt gttcagctgc ccctagtga ctccgtgtgt     780 gaagagtacg gtttgagctg ttcggatgct ctgcataatc tttttacat ctcaggtttc     840 atttcacaat gcacgcatgg agttggaagg agttcaacag acagacagtt tttctttatc     900
aaccggcggc cttgtgaccc agcaaaggtc tgcagactcg tgaatgaggt ctaccacatg     960
tataatcgac accagtatcc atttgttgtt cttaacattt ctgttgattc agaatgcgtt    1020
gatatcaatg ttactccaga taaaggcaa attttgctac aagaggaaaa gcttttgttg    1080
gcagttttaa agacctcttt gataggaatg tttgatagtg atgtcaacaa gctaaatgtc    1140
agtcagcagc cactgctgga tgttgaaggt aacttaataa aaatgcatgc agcggatttg    1200
gaaaagccca tggtagaaaa gcaggatcaa tccccttcat taaggactgg agaagaaaaa    1260
```

```
aaagacgtgt ccatttccag actgcgagag gccttttctc ttcgtcacac aacagagaac    1320
aagcctcaca gcccaaagac tccagaacca agaaggagcc ctctaggaca gaaaaggggt    1380
atgctgtctt ctagcacttc aggtgccatc tctgacaaag gcgtcctgag acctcagaaa    1440
gaggcagtga gttccagtca cggacccagt gaccctacgg acagagcgga ggtggagaag    1500
gactcggggc acggcagcac ttccgtggat tctgaggggt tcagcatccc agacacgggc    1560
agtcactgca gcagcgagta tgcggccagc tccccagggg acaggggctc gcaggaacat    1620
gtggactctc aggagaaagc gcctgaaact gacgactctt tttcagatgt ggactgccat    1680
tcaaaccagg aagataccgg atgtaaattt cgagttttgc ctcagccaac taatctcgca    1740
accccaaaca caaagcgttt taaaaaagaa gaaattcttt ccagttctga catttgtcaa    1800
aagttagtaa atactcagga catgtcagcc tctcaggttg atgtagctgt gaaaattaat    1860
aagaaagttg tgcccctgga cttttctatg agttctttag ctaaacgaat aaagcagtta    1920
catcatgaag cacagcaaag tgaaggggaa cagaattaca ggaagtttag ggcaaagatt    1980
tgtcctggag aaaatcaagc agccgaagat gaactaagaa aagagataag taaaacgatg    2040
tttgcagaaa tggaaatcat tggtcagttt aacctgggat ttataataac caaactgaat    2100
gaggatatct tcatagtgga ccagcatgcc acggacgaga agtataactt cgagatgctg    2160
cagcagcaca ccgtgctcca ggggcagagg ctcatagcac ctcagactct caacttaact    2220
gctgttaatg aagctgttct gatagaaaat ctggaaatat ttagaaagaa tggctttgat    2280
tttgttatcg atgaaaatgc tccagtcact gaaagggcta aactgatttc cttgccaact    2340
agtaaaaact ggaccttcgg accccaggac gtcgatgaac tgatcttcat gctgagcgac    2400
agccctgggg tcatgtgccg gccttcccga gtcaagcaga tgtttgcctc cagagcctgc    2460
cggaagtcgg tgatgattgg gactgctctt aacacaagcg agatgaagaa actgatcacc    2520
cacatggggg agatggacca ccctggaac tgtccccatg gaaggccaac catgagacac    2580
atcgccaacc tgggtgtcat ttctcagaac tgaccgtagt cactgtatgg aataattggt    2640
tttatcgcag atttttatgt tttgaaagac agagtcttca ctaaccttt ttgttttaaa    2700 atgaaacctg ctacttaaaa aaaatacaca tcacacccat ttaaaagtga tcttgagaac    2760
cttttcaaac c                                                        2771
```

<210> SEQ ID NO 11
<211> LENGTH: 932
<212> TYPE: PRT
<213> ORGANISM: Homo sapiens

<400> SEQUENCE: 11

```
Met Lys Gln Leu Pro Ala Ala Thr Val Arg Leu Leu Ser Ser Ser Gln
1               5                   10                  15

Ile Ile Thr Ser Val Val Ser Val Val Lys Glu Leu Ile Glu Asn Ser
                20                  25                  30

Leu Asp Ala Gly Ala Thr Ser Val Asp Val Lys Leu Glu Asn Tyr Gly
            35                  40                  45

Phe Asp Lys Ile Glu Val Arg Asp Asn Gly Glu Gly Ile Lys Ala Val
        50                  55                  60

Asp Ala Pro Val Met Ala Met Lys Tyr Tyr Thr Ser Lys Ile Asn Ser
65                  70                  75                  80

His Glu Asp Leu Glu Asn Leu Thr Thr Tyr Gly Phe Arg Gly Glu Ala
                85                  90                  95
```

-continued

```
Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys Pro Ser His Leu Gly Gln Gly Thr Thr Val Thr
    130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
            180                 185                 190

Asn Lys Ala Val Ile Trp Gln Lys Ser Arg Val Ser Asp His Lys Met
        195                 200                 205

Ala Leu Met Ser Val Leu Gly Thr Ala Val Met Asn Asn Met Glu Ser
    210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
            260                 265                 270

Leu Lys Leu Ile Arg His His Tyr Asn Leu Lys Cys Leu Lys Glu Ser
        275                 280                 285

Thr Arg Leu Tyr Pro Val Phe Phe Leu Lys Ile Asp Val Pro Thr Ala
    290                 295                 300

Asp Val Asp Val Asn Leu Thr Pro Asp Lys Ser Gln Val Leu Leu Gln
305                 310                 315                 320

Asn Lys Glu Ser Val Leu Ile Ala Leu Glu Asn Leu Met Thr Thr Cys
                325                 330                 335

Tyr Gly Pro Leu Pro Ser Thr Asn Ser Tyr Glu Asn Asn Lys Thr Asp
            340                 345                 350

Val Ser Ala Ala Asp Ile Val Leu Ser Lys Thr Ala Glu Thr Asp Val
        355                 360                 365

Leu Phe Asn Lys Val Glu Ser Ser Gly Lys Asn Tyr Ser Asn Val Asp
    370                 375                 380

Thr Ser Val Ile Pro Phe Gln Asn Asp Met His Asn Asp Glu Ser Gly
385                 390                 395                 400

Lys Asn Thr Asp Asp Cys Leu Asn His Gln Ile Ser Ile Gly Asp Phe
                405                 410                 415

Gly Tyr Gly His Cys Ser Ser Glu Ile Ser Asn Ile Asp Lys Asn Thr
            420                 425                 430

Lys Asn Ala Phe Gln Asp Ile Ser Met Ser Asn Val Ser Trp Glu Asn
        435                 440                 445

Ser Gln Thr Glu Tyr Ser Lys Thr Cys Phe Ile Ser Ser Val Lys His
    450                 455                 460

Thr Gln Ser Glu Asn Gly Asn Lys Asp His Ile Asp Glu Ser Gly Glu
465                 470                 475                 480

Asn Glu Glu Glu Ala Gly Leu Glu Asn Ser Ser Glu Ile Ser Ala Asp
                485                 490                 495

Glu Trp Ser Arg Gly Asn Ile Leu Lys Asn Ser Val Gly Glu Asn Ile
            500                 505                 510

Glu Pro Val Lys Ile Leu Val Pro Glu Lys Ser Leu Pro Cys Lys Val
```

```
                515                 520                 525
Ser Asn Asn Tyr Pro Ile Pro Glu Gln Met Asn Leu Asn Glu Asp
    530                 535                 540

Ser Cys Asn Lys Lys Ser Asn Val Ile Asp Asn Lys Ser Gly Lys Val
545                 550                 555                 560

Thr Ala Tyr Asp Leu Leu Ser Asn Arg Val Ile Lys Lys Pro Met Ser
                565                 570                 575

Ala Ser Ala Leu Phe Val Gln Asp His Arg Pro Gln Phe Leu Ile Glu
            580                 585                 590

Asn Pro Lys Thr Ser Leu Glu Asp Ala Thr Leu Gln Ile Glu Glu Leu
        595                 600                 605

Trp Lys Thr Leu Ser Glu Glu Lys Leu Lys Tyr Glu Glu Lys Ala
    610                 615                 620

Thr Lys Asp Leu Glu Arg Tyr Asn Ser Gln Met Lys Arg Ala Ile Glu
625                 630                 635                 640

Gln Glu Ser Gln Met Ser Leu Lys Asp Gly Arg Lys Lys Ile Lys Pro
                645                 650                 655

Thr Ser Ala Trp Asn Leu Ala Gln Lys His Lys Leu Lys Thr Ser Leu
            660                 665                 670

Ser Asn Gln Pro Lys Leu Asp Glu Leu Leu Gln Ser Gln Ile Glu Lys
        675                 680                 685

Arg Arg Ser Gln Asn Ile Lys Met Val Gln Ile Pro Phe Ser Met Lys
    690                 695                 700

Asn Leu Lys Ile Asn Phe Lys Lys Gln Asn Lys Val Asp Leu Glu Glu
705                 710                 715                 720

Lys Asp Glu Pro Cys Leu Ile His Asn Leu Arg Phe Pro Asp Ala Trp
                725                 730                 735

Leu Met Thr Ser Lys Thr Glu Val Met Leu Leu Asn Pro Tyr Arg Val
            740                 745                 750

Glu Glu Ala Leu Leu Phe Lys Arg Leu Leu Glu Asn His Lys Leu Pro
        755                 760                 765

Ala Glu Pro Leu Glu Lys Pro Ile Met Leu Thr Glu Ser Leu Phe Asn
    770                 775                 780

Gly Ser His Tyr Leu Asp Val Leu Tyr Lys Met Thr Ala Asp Asp Gln
785                 790                 795                 800

Arg Tyr Ser Gly Ser Thr Tyr Leu Ser Asp Pro Arg Leu Thr Ala Asn
                805                 810                 815

Gly Phe Lys Ile Lys Leu Ile Pro Gly Val Ser Ile Thr Glu Asn Tyr
            820                 825                 830

Leu Glu Ile Glu Gly Met Ala Asn Cys Leu Pro Phe Tyr Gly Val Ala
        835                 840                 845

Asp Leu Lys Glu Ile Leu Asn Ala Ile Leu Asn Arg Asn Ala Lys Glu
    850                 855                 860

Val Tyr Glu Cys Arg Pro Arg Lys Val Ile Ser Tyr Leu Glu Gly Glu
865                 870                 875                 880

Ala Val Arg Leu Ser Arg Gln Leu Pro Met Tyr Leu Ser Lys Glu Asp
                885                 890                 895

Ile Gln Asp Ile Ile Tyr Arg Met Lys His Gln Phe Gly Asn Glu Ile
            900                 905                 910

Lys Glu Cys Val His Gly Arg Pro Phe Phe His His Leu Thr Tyr Leu
        915                 920                 925

Pro Glu Thr Thr
    930
```

<210> SEQ ID NO 12
<211> LENGTH: 3063
<212> TYPE: DNA
<213> ORGANISM: Homo sapiens

<400> SEQUENCE: 12

| | | | | | |
|---|---|---|---|---|---|
| ggcacgagtg | gctgcttgcg | gctagtggat | ggtaattgcc | tgcctcgcgc | tagcagcaag | 60 |
| ctgctctgtt | aaaagcgaaa | atgaaacaat | tgcctgcggc | aacagttcga | ctcctttcaa | 120 |
| gttctcagat | catcacttcg | gtggtcagtg | ttgtaaaaga | gcttattgaa | aactccttgg | 180 |
| atgctggtgc | cacaagcgta | gatgttaaac | tggagaacta | tggatttgat | aaaattgagg | 240 |
| tgcgagataa | cggggagggt | atcaaggctg | ttgatgcacc | tgtaatggca | atgaagtact | 300 |
| acacctcaaa | aataaatagt | catgaagatc | ttgaaaattt | gacaacttac | ggttttcgtg | 360 |
| gagaagcctt | gggtcaatt | tgttgtatag | ctgaggtttt | aattacaaca | gaacggctg | 420 |
| ctgataattt | tagcacccag | tatgttttag | atggcagtgg | ccacatactt | tctcagaaac | 480 |
| cttcacatct | tggtcaaggt | acaactgtaa | ctgctttaag | attatttaag | aatctacctg | 540 |
| taagaaagca | gttttactca | actgcaaaaa | aatgtaaaga | tgaaataaaa | aagatccaag | 600 |
| atctcctcat | gagctttggt | atccttaaac | ctgacttaag | gattgtcttt | gtacataaca | 660 |
| aggcagttat | ttggcagaaa | agcagagtat | cagatcacaa | gatggctctc | atgtcagttc | 720 |
| tggggactgc | tgttatgaac | aatatggaat | cctttcagta | ccactctgaa | gaatctcaga | 780 |
| tttatctcag | tggatttctt | ccaaagtgtg | atgcagacca | ctctttcact | agtctttcaa | 840 |
| caccagaaag | aagtttcatc | ttcataaaca | gtcgaccagt | acatcaaaaa | gatatcttaa | 900 |
| agttaatccg | acatcattac | aatctgaaat | gcctaaagga | atctactcgt | ttgtatcctg | 960 |
| ttttctttct | gaaaatcgat | gttcctacag | ctgatgttga | tgtaaattta | acaccagata | 1020 |
| aaagccaagt | attattacaa | aataaggaat | ctgttttaat | tgctcttgaa | atctgatga | 1080 |
| cgacttgtta | tggaccatta | cctagtacaa | attcttatga | aataataaaa | acagatgttt | 1140 |
| ccgcagctga | catcgttctt | agtaaaacag | cagaaacaga | tgtgcttttt | aataaagtgg | 1200 |
| aatcatctgg | aaagaattat | tcaaatgttg | atacttcagt | cattccattc | caaaatgata | 1260 |
| tgcataatga | tgaatctgga | aaaaacactg | atgattgttt | aaatcaccag | ataagtattg | 1320 |
| gtgactttgg | ttatggtcat | tgtagtagtg | aaatttctaa | cattgataaa | aacactaaga | 1380 |
| atgcatttca | ggacatttca | atgagtaatg | tatcatggga | gaactctcag | acggaatata | 1440 |
| gtaaaacttg | ttttataagt | tccgttaagc | acacccagtc | agaaaatggc | aataaagacc | 1500 |
| atatagatga | gagtggggaa | aatgaggaag | aagcaggtct | tgaaaactct | tcggaaattt | 1560 |
| ctgcagatga | gtggagcagg | ggaaatatac | ttaaaaattc | agtgggagag | aatattgaac | 1620 |
| ctgtgaaaat | tttagtgcct | gaaaaaagtt | taccatgtaa | agtaagtaat | aataattatc | 1680 |
| caatccctga | acaaatgaat | cttaatgaag | attcatgtaa | caaaaaatca | aatgtaatag | 1740 |
| ataataaatc | tggaaaagtt | acagcttatg | atttacttag | caatcgagta | atcaagaaac | 1800 |
| ccatgtcagc | aagtgctctt | tttgttcaag | atcatcgtcc | tcagtttctc | atagaaaatc | 1860 |
| ctaagactag | tttagaggat | gcaacactac | aaattgaaga | actgtggaag | acattgagtg | 1920 |
| aagaggaaaa | actgaaatat | gaagagaagg | ctactaaaga | cttggaacga | tacaatagtc | 1980 |
| aaatgaagag | agccattgaa | caggagtcac | aaatgtcact | aaaagatggc | agaaaaaaga | 2040 |
| taaacccac | cagcgcatgg | aatttggccc | agaagcacaa | gttaaaaacc | tcattatcta | 2100 |

```
atcaaccaaa acttgatgaa ctccttcagt cccaaattga aaaaagaagg agtcaaaata    2160
ttaaaatggt acagatcccc tttctatga aaaacttaaa aataaatttt aagaaacaaa    2220
acaaagttga cttagaagag aaggatgaac cttgcttgat ccacaatctc aggtttcctg    2280
atgcatggct aatgacatcc aaaacagagg taatgttatt aaatccatat agagtagaag    2340
aagccctgct attaaaaga cttcttgaga atcataaact tcctgcagag ccactggaaa    2400
agccaattat gttaacagag agtctttta atggatctca ttatttagac gtttttatata   2460 aaatgacagc agatgaccaa agatacagtg gatcaactta cctgtctgat cctcgtctta    2520
cagcgaatgg tttcaagata aaattgatac caggagtttc aattactgaa aattacttgg    2580
aaatagaagg aatggctaat tgtctcccat tctatggagt agcagattta aaagaaattc    2640
ttaatgctat attaaacaga aatgcaaagg aagtttatga atgtagacct cgcaaagtga    2700
taagttattt agagggagaa gcagtgcgtc tatccagaca attacccatg tacttatcaa    2760
aagaggacat ccaagacatt atctacagaa tgaagcacca gtttggaaat gaaattaaag    2820
agtgtgttca tggtcgccca tttttcatc atttaaccta tcttccagaa actacatgat    2880
taaatatgtt taagaagatt agttaccatt gaaattggtt ctgtcataaa acagcatgag    2940 tctggttta aattatcttt gtattatgtg tcacatggtt atttttaaa tgaggattca     3000 ctgacttgtt tttatattga aaaaagttcc acgtattgta gaaacgtaa ataaactaat    3060 aac                                                                 3063

<210> SEQ ID NO 13
<211> LENGTH: 934
<212> TYPE: PRT
<213> ORGANISM: Homo sapiens

<400> SEQUENCE: 13

Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
        115                 120                 125

Ser Gln Phe Glu Asp Ile Leu Phe Gly Asn Asn Asp Met Ser Ala Ser
    130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Glu Thr Ala Gly
```

-continued

```
            195                 200                 205
Asp Met Gly Lys Leu Arg Gln Ile Ile Gln Arg Gly Ile Leu Ile
            210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Gly Glu Gln Met Asn Ser Ala
                    245                 250                 255

Val Leu Pro Glu Met Glu Asn Gln Val Ala Val Ser Ser Leu Ser Ala
                    260                 265                 270

Val Ile Lys Phe Leu Glu Leu Leu Ser Asp Asp Ser Asn Phe Gly Gln
                275                 280                 285

Phe Glu Leu Thr Thr Phe Asp Phe Ser Gln Tyr Met Lys Leu Asp Ile
        290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
                325                 330                 335

Gln Gly Gln Arg Leu Val Asn Gln Trp Ile Lys Gln Pro Leu Met Asp
                340                 345                 350

Lys Asn Arg Ile Glu Glu Arg Leu Asn Leu Val Glu Ala Phe Val Glu
                355                 360                 365

Asp Ala Glu Leu Arg Gln Thr Leu Gln Glu Asp Leu Leu Arg Arg Phe
370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
                    405                 410                 415

Val Ile Gln Ala Leu Glu Lys His Glu Gly Lys His Gln Lys Leu Leu
                420                 425                 430

Leu Ala Val Phe Val Thr Pro Leu Thr Asp Leu Arg Ser Asp Phe Ser
            435                 440                 445

Lys Phe Gln Glu Met Ile Glu Thr Thr Leu Asp Met Asp Gln Val Glu
450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
                    485                 490                 495

Ile Ser Ala Ala Arg Asp Leu Gly Leu Asp Pro Gly Lys Gln Ile Lys
                500                 505                 510

Leu Asp Ser Ser Ala Gln Phe Gly Tyr Tyr Phe Arg Val Thr Cys Lys
            515                 520                 525

Glu Glu Lys Val Leu Arg Asn Asn Lys Asn Phe Ser Thr Val Asp Ile
530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Glu Ala Gln Asp Ala
                    565                 570                 575

Ile Val Lys Glu Ile Val Asn Ile Ser Ser Gly Tyr Val Glu Pro Met
                580                 585                 590

Gln Thr Leu Asn Asp Val Leu Ala Gln Leu Asp Ala Val Val Ser Phe
            595                 600                 605

Ala His Val Ser Asn Gly Ala Pro Val Pro Tyr Val Arg Pro Ala Ile
610                 615                 620
```

-continued

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
            645                 650                 655

Phe Glu Lys Asp Lys Gln Met Phe His Ile Ile Thr Gly Pro Asn Met
            660                 665                 670

Gly Gly Lys Ser Thr Tyr Ile Arg Gln Thr Gly Val Ile Val Leu Met
            675                 680                 685

Ala Gln Ile Gly Cys Phe Val Pro Cys Glu Ser Ala Glu Val Ser Ile
690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Ile Asp Glu Leu Gly Arg
                740                 745                 750

Gly Thr Ser Thr Tyr Asp Gly Phe Gly Leu Ala Trp Ala Ile Ser Glu
                755                 760                 765

Tyr Ile Ala Thr Lys Ile Gly Ala Phe Cys Met Phe Ala Thr His Phe
770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
                820                 825                 830

Leu Ala Asn Phe Pro Lys His Val Ile Glu Cys Ala Lys Gln Lys Ala
835                 840                 845

Leu Glu Leu Glu Glu Phe Gln Tyr Ile Gly Glu Ser Gln Gly Tyr Asp
850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
                900                 905                 910

Ala Glu Val Ile Ala Lys Asn Asn Ser Phe Val Asn Glu Ile Ile Ser
            915                 920                 925

Arg Ile Lys Val Thr Thr
    930

<210> SEQ ID NO 14
<211> LENGTH: 3145
<212> TYPE: DNA
<213> ORGANISM: Homo sapiens

<400> SEQUENCE: 14
ggcgggaaac agcttagtgg gtgtggggtc gcgcattttc ttcaaccagg aggtgaggag     60
gtttcgacat ggcggtgcag ccgaaggaga cgctgcagtt ggagagcgcg gccgaggtcg    120
gcttcgtgcg cttctttcag ggcatgccgg agaagccgac caccacagtg cgccttttcg    180
accggggcga cttctatacg gcgcacggcg aggacgcgct gctggccgcc cgggaggtgt    240
tcaagaccca gggggtgatc aagtacatgg ggccggcagg agcaaagaat ctgcagagtg    300

-continued

```
ttgtgcttag taaaatgaat tttgaatctt ttgtaaaaga tcttcttctg gttcgtcagt    360
atagagttga agtttataag aatagagctg gaaataaggc atccaaggag aatgattggt    420
atttggcata taaggcttct cctggcaatc tctctcagtt tgaagacatt ctctttggta    480
acaatgatat gtcagcttcc attggtgttg tgggtgttaa aatgtccgca gttgatggcc    540
agagacaggt tggagttggg tatgtggatt ccatacagag gaaactagga ctgtgtgaat    600
tccctgataa tgatcagttc tccaatcttg aggctctcct catccagatt ggaccaaagg    660
aatgtgtttt acccggagga gagactgctg gagacatggg gaaactgaga cagataattc    720
aaagaggagg aattctgatc acagaaagaa aaaaagctga cttttccaca aaagacattt    780
atcaggacct caaccggttg ttgaaaggca aaagggaga gcagatgaat agtgctgtat    840
tgccagaaat ggagaatcag gttgcagttt catcactgtc tgcggtaatc aagttttag    900
aactcttatc agatgattcc aactttggac agtttgaact gactactttt gacttcagcc    960
agtatatgaa attggatatt gcagcagtca gagcccttaa cctttttcag ggttctgttg   1020
aagataccac tggctctcag tctctggctg ccttgctgaa taagtgtaaa accccctcaag  1080
gacaaagact tgttaaccag tggattaagc agcctctcat ggataagaac agaatagagg   1140
agagattgaa tttagtggaa gcttttgtag aagatgcaga attgaggcag actttacaag   1200
aagatttact tcgtcgattc ccagatctta accgacttgc caagaagttt caaagacaag   1260
cagcaaactt acaagattgt taccgactct atcagggtat aaatcaacta cctaatgtta   1320
tacaggctct ggaaaaacat gaaggaaaac accagaaatt attgttggca gttttttgtga 1380
ctcctcttac tgatcttcgt tctgacttct ccaagtttca ggaaatgata gaaacaactt   1440
tagatatgga tcaggtggaa aaccatgaat tccttgtaaa accttcattt gatcctaatc   1500
tcagtgaatt aagagaaata atgaatgact tggaaaagaa gatgcagtca acattaataa   1560
gtgcagccag gatcttggc ttggaccctg gcaaacagat taaactggat tccagtgcac    1620
agtttggata ttactttcgt gtaacctgta aggaagaaaa agtccttcgt aacaataaaa   1680
actttagtac tgtagatatc cagaagaatg gtgttaaatt taccaacagc aaattgactt   1740
cttttaaatga agagtatacc aaaaataaaa cagaatatga agaagcccag gatgccattg   1800
ttaaagaaat tgtcaatatt tcttcaggct atgtagaacc aatgcagaca ctcaatgatg   1860
tgttagctca gctagatgct gttgtcagct ttgctcacgt gtcaaatgga gcacctgttc   1920
catatgtacg accagccatt ttggagaaag gacaaggaag aattatatta aaagcatcca   1980
ggcatgcttg tgttgaagtt caagatgaaa ttgcattat tcctaatgac gtatactttg   2040
aaaaagataa acagatgttc cacatcatta ctggccccaa tatgggaggt aaatcaacat   2100
atattcgaca aactggggtg atagtactca tggcccaaat tgggtgtttt gtgccatgtg   2160
agtcagcaga agtgtccatt gtggactgca tcttagcccg gtagggggct ggtgacagtc   2220
aattgaaagg agtctccacg ttcatggctg aaatgttgga aactgcttct atcctcaggt   2280
ctgcaaccaa agattcatta ataatcatag atgaattggg aagaggaact tctacctacg   2340
atggatttgg gttagcatgg gctatatcag aatacattgc aacaaagatt ggtgcttttt   2400
gcatgtttgc aacccatttt catgaactta ctgccttggc caatcagata ccaactgtta   2460
ataatctaca tgtcacagca ctcaccactg aagagacctt aactatgctt tatcaggtga   2520
agaaaggtgt ctgtgatcaa agttttggga ttcatgttgc agagcttgct aatttcccta   2580
agcatgtaat agagtgtgct aaacagaaag ccctggaact tgaggagttt cagtatattg   2640
gagaatcgca aggatatgat atcatggaac cagcagcaaa gaagtgctat ctggaaagag   2700
```

```
agcaaggtga aaaaattatt caggagttcc tgtccaaggt gaaacaaatg cccttactg      2760 aaatgtcaga agaaaacatc acaataaagt taaaacagct aaaagctgaa gtaatagcaa    2820
agaataatag ctttgtaaat gaaatcattt cacgaataaa agttactacg tgaaaaatcc    2880
cagtaatgga atgaaggtaa tattgataag ctattgtctg taatagtttt atattgtttt    2940
atattaaccc ttttttccata gtgttaactg tcagtgccca tgggctatca acttaataag   3000
atatttagta atattttact ttgaggacat tttcaaagat ttttattttg aaaaatgaga    3060
gctgtaactg aggactgttt gcaattgaca taggcaataa taagtgatgt gctgaatttt    3120
ataaataaaa tcatgtagtt tgtgg                                          3145
```

<210> SEQ ID NO 15
<211> LENGTH: 756
<212> TYPE: PRT
<213> ORGANISM: Homo sapiens

<400> SEQUENCE: 15

```
Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
                20                  25                  30

Lys Glu Met Ile Glu Asn Cys Leu Asp Ala Lys Ser Thr Ser Ile Gln
            35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
                100                 105                 110

Val Thr Ile Thr Thr Lys Thr Ala Asp Gly Lys Cys Ala Tyr Arg Ala
            115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
                180                 185                 190

Ser Val Lys Lys Gln Gly Glu Thr Val Ala Asp Val Arg Thr Leu Pro
            195                 200                 205

Asn Ala Ser Thr Val Asp Asn Ile Arg Ser Ile Phe Gly Asn Ala Val
    210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
                260                 265                 270

Arg Lys Ala Ile Glu Thr Val Tyr Ala Ala Tyr Leu Pro Lys Asn Thr
            275                 280                 285
```

-continued

```
His Pro Phe Leu Tyr Leu Ser Leu Glu Ile Ser Pro Gln Asn Val Asp
    290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
        355                 360                 365

Ser Ser Thr Ser Gly Ser Ser Asp Lys Val Tyr Ala His Gln Met Val
370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
        435                 440                 445

Gly Asp Thr Thr Lys Gly Thr Ser Glu Met Ser Glu Lys Arg Gly Pro
450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
        515                 520                 525

Ser Phe Val Gly Cys Val Asn Pro Gln Trp Ala Leu Ala Gln His Gln
530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Asp Gly Pro Lys Glu Gly Leu Ala
        595                 600                 605

Glu Tyr Ile Val Glu Phe Leu Lys Lys Lys Ala Glu Met Leu Ala Asp
610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
            660                 665                 670

Phe Glu Ser Leu Ser Lys Glu Cys Ala Met Phe Tyr Ser Ile Arg Lys
        675                 680                 685

Gln Tyr Ile Ser Glu Glu Ser Thr Leu Ser Gly Gln Gln Ser Glu Val
        690                 695                 700

Pro Gly Ser Ile Pro Asn Ser Trp Lys Trp Thr Val Glu His Ile Val
```

|     | 705 |     |     |     | 710 |     |     |     | 715 |     |     |     | 720 |
| --- | --- | --- | --- | --- | --- | --- | --- | --- | --- | --- | --- | --- | --- |

Tyr Lys Ala Leu Arg Ser His Ile Leu Pro Pro Lys His Phe Thr Glu
                            725                        730                        735

Asp Gly Asn Ile Leu Gln Leu Ala Asn Leu Pro Asp Leu Tyr Lys Val
              740                        745                        750

Phe Glu Arg Cys
        755

<210> SEQ ID NO 16
<211> LENGTH: 2484
<212> TYPE: DNA
<213> ORGANISM: Homo sapiens

<400> SEQUENCE: 16

| | | | | | |
|---|---|---|---|---|---|
| cttggctctt | ctggcgccaa | aatgtcgttc | gtggcagggg | ttattcggcg | gctggacgag | 60 |
| acagtggtga | accgcatcgc | ggcggggaa | gttatccagc | ggccagctaa | tgctatcaaa | 120 |
| gagatgattg | agaactgttt | agatgcaaaa | tccacaagta | ttcaagtgat | tgttaaagag | 180 |
| ggaggcctga | agttgattca | gatccaagac | aatggcaccg | ggatcaggaa | agaagatctg | 240 |
| gatattgtat | gtgaaaggtt | cactactagt | aaactgcagt | cctttgagga | tttagccagt | 300 |
| atttctacct | atggctttcg | aggtgaggct | ttggccagca | taagccatgt | ggctcatgtt | 360 |
| actattacaa | cgaaaacagc | tgatggaaag | tgtgcataca | gagcaagtta | ctcagatgga | 420 |
| aaactgaaag | cccctcctaa | accatgtgct | ggcaatcaag | ggacccagat | cacggtggag | 480 |
| gaccttttt | acaacatagc | cacgaggaga | aaagctttaa | aaaatccaag | tgaagaatat | 540 |
| gggaaaattt | tggaagttgt | tggcaggtat | tcagtacaca | atgcaggcat | tagtttctca | 600 |
| gttaaaaaac | aaggagagac | agtagctgat | gttaggacac | tacccaatgc | ctcaaccgtg | 660 |
| gacaatattc | gctccatctt | tggaaatgct | gttagtcgag | aactgataga | aattggatgt | 720 |
| gaggataaaa | ccctagcctt | caaaatgaat | ggttacatat | ccaatgcaaa | ctactcagtg | 780 |
| aagaagtgca | tcttcttact | cttcatcaac | catcgtctgg | tagaatcaac | ttccttgaga | 840 |
| aaagccatag | aaacagtgta | tgcagcctat | ttgcccaaaa | acacacaccc | attcctgtac | 900 |
| ctcagtttag | aaatcagtcc | ccagaatgtg | atgttaatg | tgcaccccac | aaagcatgaa | 960 |
| gttcacttcc | tgcacgagga | gagcatcctg | agcgggtgc | agcagcacat | cgagagcaag | 1020 |
| ctcctgggct | ccaattcctc | caggatgtac | ttcacccaga | ctttgctacc | aggacttgct | 1080 |
| ggcccctctg | ggagatggt | taaatccaca | acaagtctga | cctcgtcttc | tacttctgga | 1140 |
| agtagtgata | aggtctatgc | ccaccagatg | gttcgtacag | attcccggga | acagaagctt | 1200 |
| gatgcatttc | tgcagcctct | gagcaaaccc | ctgtccagtc | agcccaggc | cattgtcaca | 1260 |
| gaggataaga | cagatatttc | tagtggcagg | gctaggcagc | aagatgagga | gatgcttgaa | 1320 |
| ctcccagccc | ctgctgaagt | ggctgccaaa | atcagagct | tggagggga | tacaacaaag | 1380 |
| gggacttcag | aaatgtcaga | agagagga | cctacttcca | gcaacccag | aaagagacat | 1440 |
| cgggaagatt | ctgatgtgga | aatggtggaa | gatgattccc | gaaaggaaat | gactgcagct | 1500 |
| tgtaccccc | ggagaaggat | cattaacctc | actagtgttt | tgagtctcca | ggaagaaatt | 1560 |
| aatgagcagg | gacatgaggt | tctccgggag | atgttgcata | accactcctt | cgtgggctgt | 1620 |
| gtgaatcctc | agtgggcctt | ggcacagcat | caaaccaagt | tataccttct | caacaccacc | 1680 |
| aagcttagtg | aagaactgtt | ctaccagata | ctcatttatg | attttgccaa | ttttggtgtt | 1740 |
| ctcaggttat | cggagccagc | accgctcttt | gaccttgcca | tgcttgcctt | agatagtcca | 1800 |

-continued

```
gagagtggct ggacagagga agatggtccc aaagaaggac ttgctgaata cattgttgag    1860
tttctgaaga agaaggctga gatgcttgca gactatttct ctttggaaat tgatgaggaa    1920
gggaacctga ttggattacc ccttctgatt gacaactatg tgcccccttt ggagggactg    1980
cctatcttca ttcttcgact agccactgag gtgaattggg acgaagaaaa ggaatgtttt    2040
gaaagcctca gtaaagaatg cgctatgttc tattccatcc ggaagcagta catatctgag    2100
gagtcgaccc tctcaggcca gcagagtgaa gtgcctggct ccattccaaa ctcctggaag    2160
tggactgtgg aacacattgt ctataaagcc ttgcgctcac acattctgcc tcctaaacat    2220
ttcacagaag atggaaatat cctgcagctt gctaacctgc ctgatctata caaagtcttt    2280
gagaggtgtt aaatatggtt atttatgcac tgtgggatgt gttcttcttt ctctgtattc    2340
cgatacaaag tgttgtatca agtgtgata tacaaagtgt accaacataa gtgttggtag    2400
cacttaagac ttatacttgc cttctgatag tattcccttta tacacagtgg attgattata    2460
aataaataga tgtgtcttaa cata                                          2484
```

<210> SEQ ID NO 17
<211> LENGTH: 133
<212> TYPE: PRT
<213> ORGANISM: Homo sapiens

<400> SEQUENCE: 17

```
Met Glu Arg Ala Glu Ser Ser Thr Glu Pro Ala Lys Ala Ile Lys
1               5                   10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
        35                  40                  45

Ala Gly Ala Thr Asn Ile Asp Leu Lys Leu Lys Asp Tyr Gly Val Asp
    50                  55                  60

Leu Ile Glu Val Ser Asp Asn Gly Cys Gly Val Glu Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr
    130
```

<210> SEQ ID NO 18
<211> LENGTH: 426
<212> TYPE: DNA
<213> ORGANISM: Homo sapiens

<400> SEQUENCE: 18

```
cgaggcggat cgggtgttgc atccatggag cgagctgaga gctcgagtac agaacctgct     60
aaggccatca aacctattga tcggaagtca gtccatcaga tttgctctgg gcaggtggta    120
ctgagtctaa gcactgcggt aaaggagtta gtagaaaaca gtctggatgc tggtgccact    180
aatattgatc taaagcttaa ggactatgga gtggatctta ttgaagtttc agacaatgga    240 tgtgggggtag aagaagaaaa cttcgaaggc ttaactctga acatcacac atctaagatt    300 caagagtttg ccgacctaac tcaggttgaa acttttggct tcggggggga agctctgagc    360
```

```
-continued tcactttgtg cactgagcga tgtcaccatt tctacctgcc acgcatcggc gaaggttgga    420
acttga                                                              426
```